United States Patent
Takahashi et al.

(10) Patent No.: US 12,285,156 B2
(45) Date of Patent: Apr. 29, 2025

(54) BALLOON MOUNTING JIG

(71) Applicant: FUJIFILM Corporation, Tokyo (JP)

(72) Inventors: Nobuharu Takahashi, Kanagawa (JP); Ayumu Kawashima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 478 days.

(21) Appl. No.: 17/881,554

(22) Filed: Aug. 4, 2022

(65) Prior Publication Data

US 2022/0369898 A1 Nov. 24, 2022

Related U.S. Application Data

(63) Continuation of application No. PCT/JP2021/006661, filed on Feb. 22, 2021.

(30) Foreign Application Priority Data

Feb. 28, 2020 (JP) ................ 2020-033961

(51) Int. Cl.
*A61B 1/00* (2006.01)

(52) U.S. Cl.
CPC ........ *A61B 1/0011* (2013.01); *A61B 1/00082* (2013.01)

(58) Field of Classification Search
CPC .............. A61B 1/00082; A61B 1/0011; A61B 1/00135; A61B 1/00137; A61B 1/00142
See application file for complete search history.

(56) References Cited

U.S. PATENT DOCUMENTS

2006/0111610 A1   5/2006   Machida

FOREIGN PATENT DOCUMENTS

| CN | 1771880 | 5/2006 |
|---|---|---|
| JP | H08173424 | 7/1996 |
| JP | 2006150103 | 6/2006 |
| JP | 2006230777 | 9/2006 |
| JP | 2007330467 | 12/2007 |
| JP | 2009011656 | 1/2009 |
| JP | 2009028350 | 2/2009 |
| JP | 2010017485 | 1/2010 |

(Continued)

OTHER PUBLICATIONS

"International Search Report (Form PCT/ISA/210) of PCT/JP2021/006661," mailed on Apr. 20, 2021, with English translation thereof, pp. 1-6.

(Continued)

*Primary Examiner* — Timothy J Neal
(74) *Attorney, Agent, or Firm* — JCIPRNET

(57) ABSTRACT

An object is to provide a balloon mounting jig capable of reducing the burden of an operation of mounting a balloon in an insertion part of an endoscope. A balloon mounting jig (100) for mounting a balloon (60) including a first sleeve part (60A), a second sleeve part (60B), and a balloon main body (60C), to an insertion part (12) of an endoscope (10) or an insertion assisting tool, the balloon mounting jig (100) including: a main body (102) formed in a hollow cylindrical shape to be folded flat and having a first opening part (104) and a second opening part (106); a pair of guide pieces (108a, 108b) that face each other and are provided in the second opening part (106). A sliding surface (120) on which an outer peripheral surface of the insertion part (12) or the insertion assisting tool is slidable is provided on inner surfaces of the main body (102) and the pair of guide pieces (108a, 108b).

11 Claims, 15 Drawing Sheets

(56) References Cited

FOREIGN PATENT DOCUMENTS

| | | |
|---|---|---|
| JP | 2011245012 | 12/2011 |
| JP | 2020163114 | 10/2020 |

OTHER PUBLICATIONS

"International Preliminary Report on Patentability (Form PCT/IPEA/409) of PCT/JP2021/006661," completed on Jan. 31, 2022, with English translation thereof, pp. 1-6.
"Office Action of China Counterpart Application", with English translation thereof, issued on Oct. 24, 2024, pp. 1-10.

FIG. 6
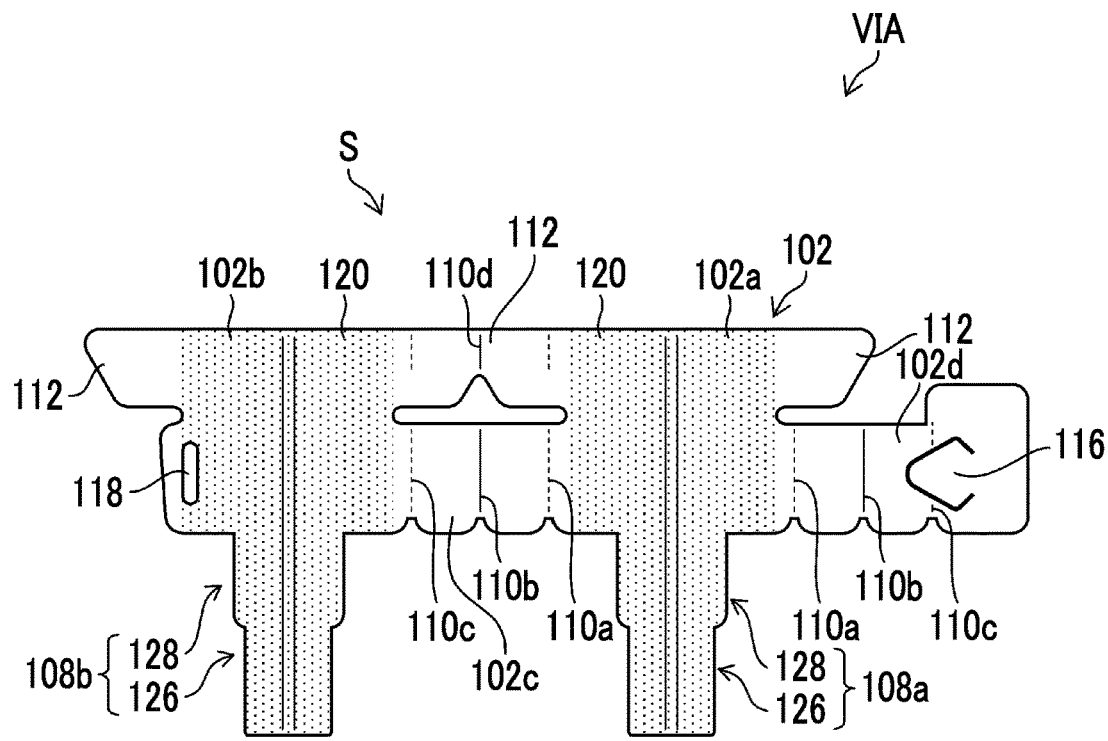
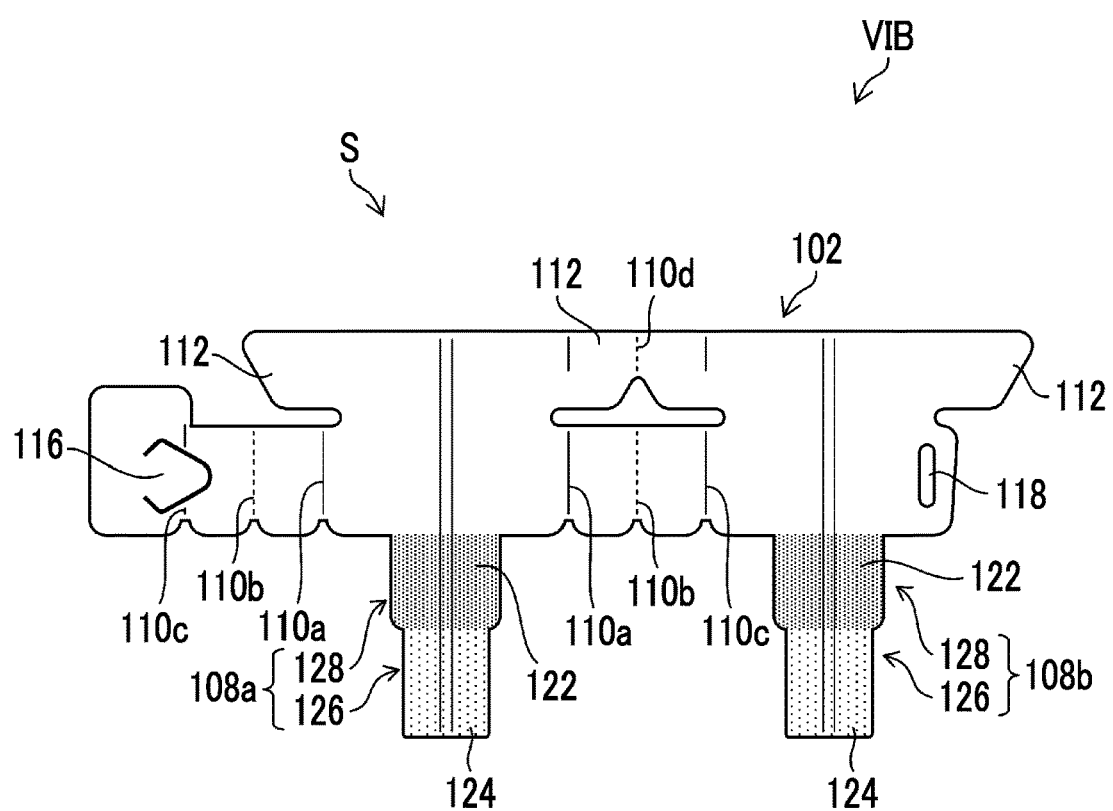

BALLOON MOUNTING JIG

CROSS-REFERENCE TO RELATED APPLICATIONS

The present application is a Continuation of PCT International Application No. PCT/JP2021/006661 filed on Feb. 22, 2021 claiming priority under 35 U.S.C § 119(a) to Japanese Patent Application No. 2020-033961 filed on Feb. 28, 2020. Each of the above applications is hereby expressly incorporated by reference, in its entirety, into the present application.

BACKGROUND OF THE INVENTION

1. Field of the Invention

The present invention relates to a balloon mounting jig, and more particularly, to a balloon mounting jig for mounting a balloon to an insertion part of an endoscope or an insertion assisting tool that serves as a guide in a case where the insertion part is inserted into a body cavity.

2. Description of the Related Art

In endoscope apparatuses, balloons that expand and contract are used in various applications. For example, in an endoscope apparatus for observing a deep digestive tract such as the small intestine or the large intestine, an inflatable balloon is mounted to an insertion part of an endoscope, and it is possible to fix the insertion part of the endoscope inside a body by expanding the balloon.

Such a balloon is made of an elastic body such as rubber, and its end part is formed in a cylindrical shape having a smaller diameter than an outer diameter of a mounting target (the insertion part of the endoscope) in a natural state. Further, in mounting the balloon, after covering the mounting target with the balloon while expanding the diameter of the end part of the balloon, the end part of the balloon is fixed to the mounting target by winding thread from the top of the end part of the balloon or externally fitting a rubber band onto the end part of the balloon.

However, there is a problem that an operation of covering the mounting target with the balloon while expanding the diameter of the end part of the balloon is very troublesome and takes time and effort. For example, JP2009-11656A discloses a balloon mounting jig comprising first and second guide pieces that are inserted into sleeve parts that are provided at both end parts of a balloon main body. The balloon mounting jig is configured so that an insertion part of an endoscope is inserted between the first guide piece and the second guide piece to insert an endoscope into the sleeve parts of the balloon.

SUMMARY OF THE INVENTION

However, the mounting jig described in JP2009-11656A moves the balloon on the insertion part by gripping the first guide piece and the second guide piece in a state where the sleeve parts of the balloon are covered on the first guide piece and the second guide piece, and the balloon is dragged by a frictional force between the insertion part and the balloon, so that there is a problem that wrinkles are likely to occur on the balloon. Further, there is a problem that it is difficult to move the first guide piece and the second guide piece because of a tension of the balloon. Further, there is a problem that a position of the balloon easily shifts when the first guide piece and the second guide piece are pulled out from the balloon after moving the balloon to a predetermined position of the insertion part.

The present invention has been made in consideration of the above-mentioned problems, and an object of the present invention is to provide a balloon mounting jig capable of reducing the burden of an operation of mounting a balloon in an insertion part of an endoscope.

In order to achieve the object of the present invention, there is provided a balloon mounting jig for mounting a balloon including a balloon main body, a first sleeve part provided at one end of the balloon main body, and a second sleeve part provided at the other end on a side opposite to the first sleeve part while interposing the balloon main body, to an insertion part of an endoscope or an insertion assisting tool that assists an insertion of the insertion part of the endoscope into a body cavity, the balloon mounting jig including: a main body formed in a hollow cylindrical shape to be folded flat and having a first opening part at one end thereof and a second opening part at the other end thereof; and a pair of guide pieces that face each other and are provided so as to extend from the second opening part toward a side opposite to a side where the first opening part is provided, in which a sliding surface on which an outer peripheral surface of the insertion part or the insertion assisting tool is slidable is provided on inner surfaces of the main body and the pair of guide pieces.

In one embodiment of the present invention, it is preferable that the sliding surface is a region where at least the insertion part or the insertion assisting tool is in contact with the main body and the pair of guide pieces.

In one embodiment of the present invention, it is preferable that the sliding surface is an entire region of the inner surfaces of the main body and the pair of guide pieces.

In one embodiment of the present invention, it is preferable that the sliding surface has a smaller friction coefficient than outer surfaces of the main body and the pair of guide pieces.

In one embodiment of the present invention, it is preferable that the sliding surface is a wrinkled uneven surface.

In one embodiment of the present invention, it is preferable that the sliding surface has a coating layer made of a plastic material.

In one embodiment of the present invention, it is preferable that the pair of guide pieces include a high friction part provided on an outer surface of the guide piece on a second opening part side, and a low friction part provided on an outer surface of the guide piece on a distal end side and having a smaller friction coefficient than the high friction part.

In one embodiment of the present invention, it is preferable that the high friction part has a smooth surface sheet or a pressure-sensitive adhesive coating layer.

In one embodiment of the present invention, it is preferable that the pair of guide pieces each has a narrow part provided on a distal end side of the guide piece, and a wide part provided on a second opening part side of the guide piece and wider than the narrow part, and a total length of widths of the wide parts of the pair of guide pieces is equal to or less than a length of an outer periphery of the insertion part or the insertion assisting tool.

In order to achieve the object of the present invention, there is provided a balloon mounting jig for mounting a balloon including a balloon main body, a first sleeve part provided at one end of the balloon main body, and a second sleeve part provided at the other end on a side opposite to the first sleeve part while interposing the balloon main body, to an insertion part of an endoscope or an insertion assisting tool that assists an insertion of the insertion part of the endoscope into a body cavity, the balloon mounting jig including: a main body formed in a hollow cylindrical shape to be folded flat and having a first opening part at one end thereof and a second opening part at the other end thereof; a pair of guide pieces that face each other and are provided so as to extend from the second opening part toward a side opposite to a side where the first opening part is provided; and a narrow part on a distal end side of the guide piece and a wide part wider than the narrow part on a second opening part side, which are provided in the pair of guide pieces, in which a total length of widths of the wide parts of the pair of guide pieces is equal to or less than a length of an outer periphery of the insertion part or the insertion assisting tool.

In one embodiment of the present invention, it is preferable that a material of the main body and the pair of guide pieces is a resin or paper.

According to the balloon mounting jig of the present invention, the balloon mounting jig can be easily moved with respect to the insertion part, the balloon mounting jig can be easily extracted from the endoscope to which the balloon is mounted, and the balloon mounting jig integrated with the balloon can be easily moved.

BRIEF DESCRIPTION OF THE DRAWINGS

FIG. 6 is a plan view of a sheet for constituting the balloon mounting jig.

DESCRIPTION OF THE PREFERRED EMBODIMENTS

Hereinafter, a balloon mounting jig according to an embodiment of the present invention will be described with reference to the accompanying drawings.

Figure 1:
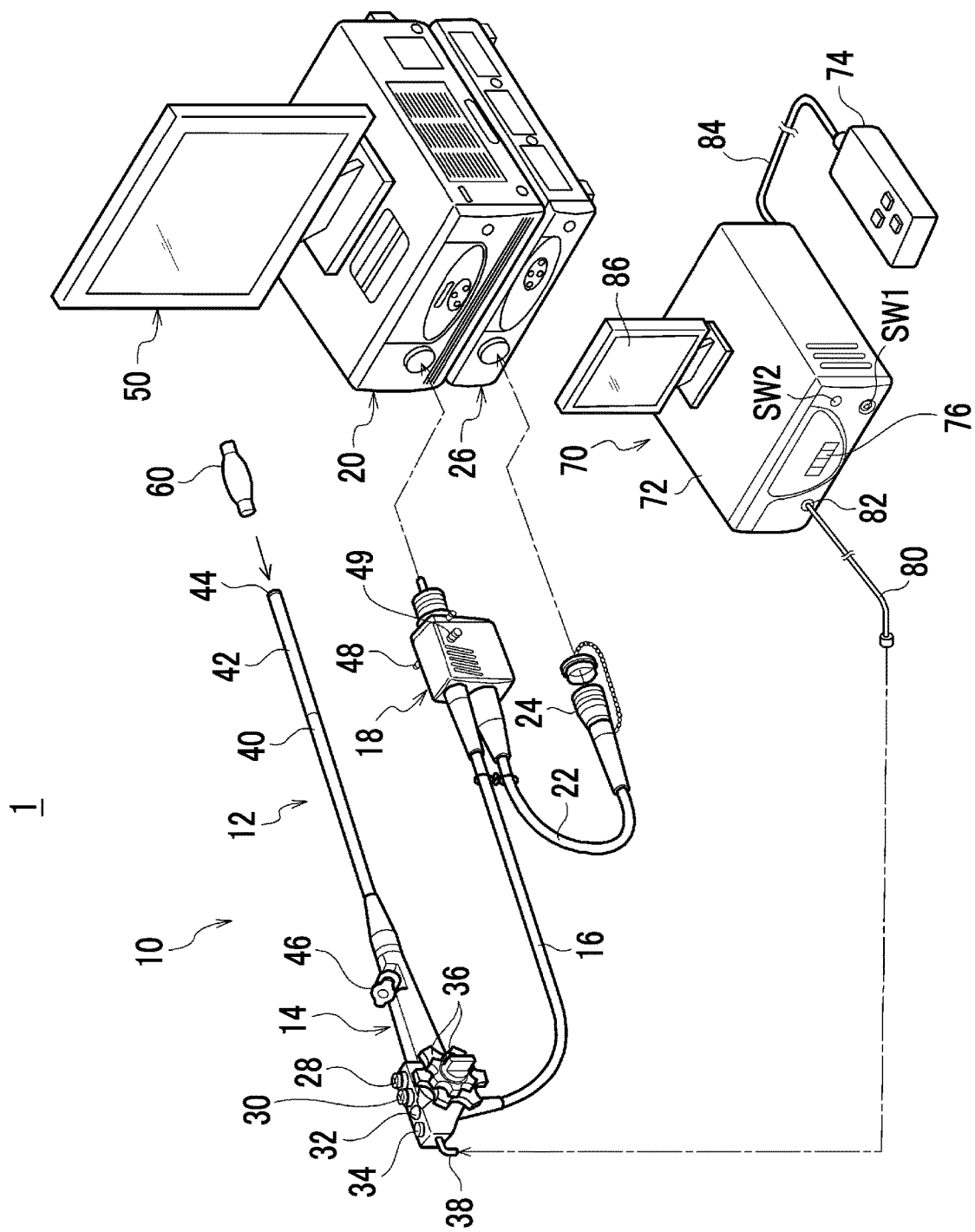
FIG. 1 is a diagram showing a system configuration of an endoscope apparatus using a balloon.

FIG. 1 is a system configuration diagram showing an example of an endoscope using a balloon mounted by using the balloon mounting jig according to the embodiment of the present invention. As shown in FIG. 1, an endoscope apparatus mainly includes an endoscope 10, a balloon 60, and a balloon control device 70 as main components.

The endoscope 10 comprises an operation part 14 and an insertion part 12 that is connected to the operation part 14 and is inserted into a body. A universal cord 16 is connected to the operation part 14, and an LG connector 18 is provided at a distal end of the universal cord 16. The LG connector 18 is detachably connected to a light source device 20, and thus, illumination light is sent to an illumination window (not shown) provided at the distal end of the insertion part 12. Further, an electric connector 24 is connected to the LG connector 18 through a cable 22, and the electric connector 24 is detachably connected to a processor 26.

An air/water supply button 28, a suction button 30, a shutter button 32, and a function switching button 34 are provided in parallel in the operation part 14, and a pair of angle knobs 36 and 36 are also provided therein.

The insertion part 12 includes a flexible part 40, a bendable part 42, and a distal end part 44 in order from a side of the operation part 14. The flexible part 40 is configured by covering an outer periphery of a metal plate wound in a spiral shape with a net and coating the outer periphery, and has sufficient flexibility.

The bendable part 42 is configured to be bent remotely by rotating the angle knobs 36 and 36 of the operation part 14. For example, the bendable part 42 is configured so that a plurality of cylindrical nodal rings are connected to be rotatable using pins and a plurality of operation wires are inserted into the nodal rings to be guided by the pins. Further, by pushing and pulling the operation wires, the nodal rings are rotated to bend the bendable part 42. By bending the bendable part 42, it is possible to direct the distal end part 44 in a desired direction.

Figure 2:
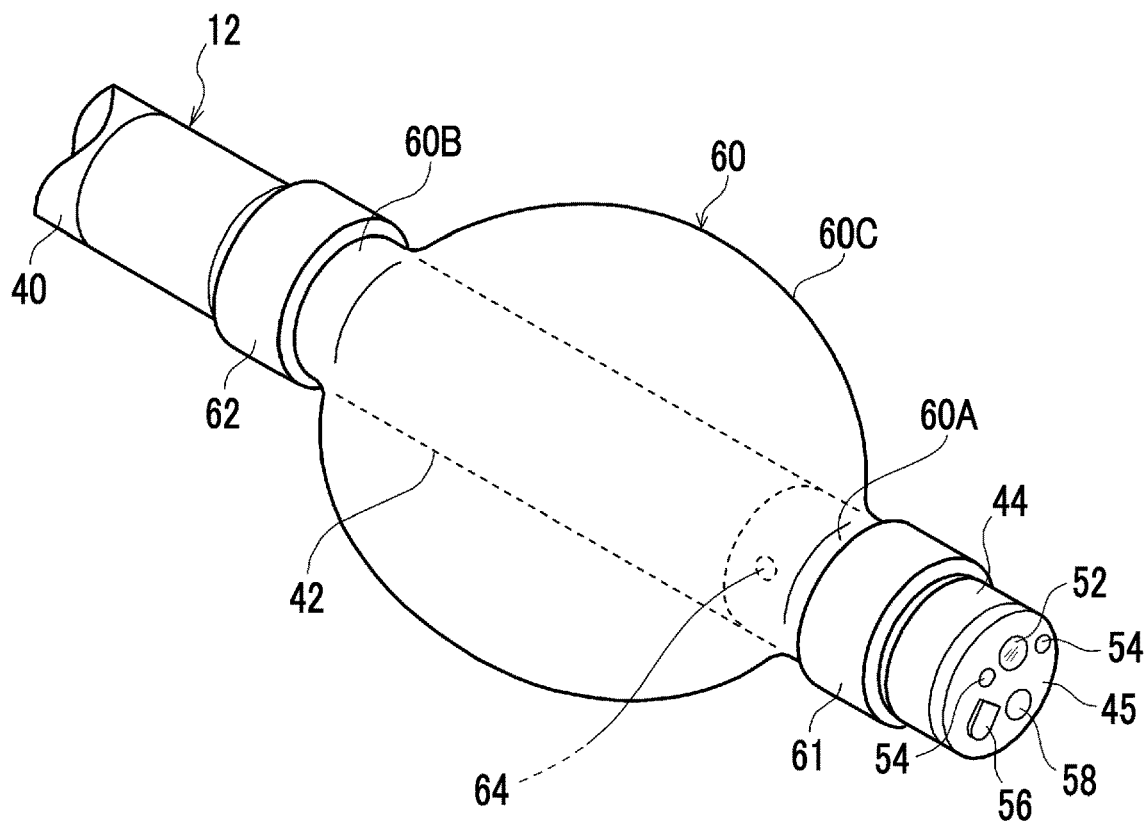
FIG. 2 is a perspective view showing a distal end part of an insertion part of an endoscope.

As shown in FIG. 2, an observation window 52, illumination windows 54 and 54, an air/water supply nozzle 56, and a forceps port 58 are provided on a distal end surface of the distal end part 44. An observation optical system and an imaging element such as a complementary metal oxide semiconductor (CMOS) and a charge coupled device (CCD) are disposed behind the observation window 52, and a signal cable is connected to a substrate that supports the imaging element. The signal cable is inserted into the insertion part 12, the operation part 14, the universal cord 16, or the like to be extended to the electric connector 24, and is connected to the processor 26. Accordingly, an observation image received by the observation window 52 is formed on a light receiving surface of the imaging element, and is converted into an electric signal. The electric signal is output to the processor 26 through the signal cable and is converted into a video signal. Thus, the observation image is displayed on the monitor 50 connected to the processor 26.

The illumination window 54 is configured so that an illumination optical system and an emitting end of a light guide (not shown) are disposed behind the illumination window 54. The light guide is inserted into the insertion part 12, the operation part 14, and the universal cord 16, and an incident end of the light guide is disposed in the LG connector 18. Accordingly, by connecting the LG connector 18 to the light source device 20, illumination light emitted from the light source device 20 is transmitted to the illumination optical system through the light guide and is emitted forward from the illumination window 54.

The air/water supply nozzle 56 provided at the distal end part 44 communicates with a valve (not shown) operated by the air/water supply button 28. The valve communicates with an air/water supply connector 48 provided in the LG connector 18. Air/water supply means (not shown) is connected to the air/water supply connector 48 to supply air and water. Accordingly, by operating the air/water supply button 28, air or water is jetted from the air/water supply nozzle 56 toward the observation window 52.

The forceps port 58 provided at the distal end part 44 communicates with a forceps insertion part 46. Accordingly, by inserting a treatment tool such as forceps through the forceps insertion part 46, it is possible to draw out the treatment tool from the forceps port 58. Further, the forceps port 58 communicates with a valve (not shown) operated by the suction button 30, and the valve is connected to the suction connector 49 of the LG connector 18. Accordingly, by connecting suction means (not shown) to the suction connector 49 and performing an operation using the suction button 30, it is possible to suction a lesion portion or the like through the forceps port 58.

The balloon 60 is detachably mounted on the outer periphery of the insertion part 12 of the endoscope 10. The balloon 60 is made of an elastic material such as silicone rubber. The balloon 60 includes a first sleeve part 60A provided at one end thereof, a second sleeve part 60B provided at the other end thereof, and a balloon main body 60C provided between the first sleeve part 60A and the second sleeve part 60B, in which the first sleeve part 60A and the second sleeve part 60B are formed in an approximately cylindrical shape that is narrowed with respect to the balloon main body 60C.

The balloon 60 is disposed at a predetermined mounting position (for example, from the distal end part 44 to the bendable part 42) by causing the insertion part 12 to pass therethrough. The first sleeve part 60A and the second sleeve part 60B are formed to have an inner diameter smaller than an outer diameter of the insertion part 12 of the endoscope 10 in a natural state. In a case where the balloon 60 is mounted on the insertion part 12, an elastic force of the first sleeve part 60A and an elastic force of the second sleeve part 60B act inward in a radial direction of the insertion part 12. The balloon 60 is retained at a predetermined position of the insertion part 12 by the elastic forces.

A rubber band that is a cylindrical first balloon fixing member 61 is fitted on an outer periphery of the first sleeve part 60A, and a rubber band that is a cylindrical second balloon fixing member 62 is fitted on an outer periphery of the second sleeve part 60B. The balloon 60 is fixed to the insertion part 12 by the first balloon fixing member 61 and the second balloon fixing member 62. The balloon 60 is mounted by using the balloon mounting jig according to the embodiment of the present invention. The balloon mounting jig will be described later.

A ventilation hole 64 is formed at the balloon mounting position of the insertion part 12, and the ventilation hole 64 communicates with a balloon air supply port 38 of the operation part 14 shown in FIG. 1. A tube 80 shown in FIG. 1 is connected to the balloon air supply port 38, and the balloon control device 70 is connected to the balloon air supply port 38 through the tube 80. The balloon control device 70 is a device that supplies and suctions fluid such as air into the balloon 60. By supplying and suctioning fluid (for example, air) from the balloon control device 70, it is possible to supply and suction air into the balloon 60. The balloon 60 expands into a substantially spherical shape by being supplied with air, and sticks to the outer surface of the insertion part 12 by suctioning air.

As shown in FIG. 1, the balloon control device 70 includes a device main body 72 and a hand switch 74 for remote control, as main components. On a front surface of the device main body 72, a power switch SW1, a stop switch SW2, and a pressure display unit 76 are provided. The pressure display unit 76 is a panel that displays a pressure value of the balloon 60, and an error code is displayed on the pressure display unit 76 in a case where an abnormality such as balloon breakage occurs.

The tube 80 that performs the supply and suction of air into the balloon 60 is connected to the front surface of the device main body 72. A connection portion between the tube 80 and the device main body 72 is provided with a backflow prevention unit 82 for preventing backflow of a body fluid in a case where the balloon 60 is broken. The backflow prevention unit 82 is configured by incorporating a gas-liquid separation filter in a hollow disk-like case (not shown) that is detachably mounted to the device main body 72, in which inflow of fluid in the device main body 72 is prevented by the filter.

On the other hand, the hand switch 74 is provided with various switches. For example, a stop switch similar to the stop switch SW2 on the side of the device main body 72, an ON/OFF switch for instructing pressurization and decompression of the balloon 60, a pause switch for retaining the pressure of the balloon 60, or the like are provided. The hand switch 74 is electrically connected to the device main body 72 through a cord 84. Although not shown in FIG. 1, the hand switch 74 is provided with a display unit that indicates an air supply state or an exhaust state of the balloon 60.

The balloon control device 70 causes air to be supplied to the balloon 60 to expand the balloon 60, and controls the air pressure at a constant value to retain the balloon 60 in an expanded state. Further, the balloon control device 70 causes air to be suctioned from the balloon 60 to contract the balloon 60, and controls the air pressure at a constant value to retain the balloon 60 in a contracted state.

The balloon control device 70 is connected to a balloon dedicated monitor 86, and displays the pressure value and the expanded and contracted state of the balloon 60 on the balloon dedicated monitor 86 in a case where the balloon 60 is expanded and contracted. The pressure value and the expanded and contracted state of the balloon 60 may be displayed on the monitor 50 to be superimposed on the observation image of the endoscope 10.

As an example of the operation method of the endoscope apparatus, the insertion part 12 is inserted in a pushing manner, and the balloon 60 is expanded as necessary to fix the insertion part 12 in the body (for example, the large intestine). Further, after the insertion part 12 is pulled to simplify a tubular shape of the body (for example, the large intestine), the balloon 60 is contracted, and the insertion part 12 is further inserted into a deep part of the intestinal tract. For example, the insertion part 12 is inserted from the subject's anus, and in a case where the distal end of the insertion part 12 passes the sigmoid colon, the balloon 60 is expanded to fix the insertion part 12 to the intestinal tract, and the insertion part 12 is pulled to form the sigmoid colon in a substantially linear shape. Further, the balloon 60 is contracted and the distal end of the insertion part 12 is inserted into a deep part of the intestinal tract. Accordingly, it is possible to insert the insertion part 12 in the deep part of the intestinal tract. The above-described endoscope 10 may be used as a double balloon type endoscope apparatus together with an insertion assisting tool (not shown) with a balloon mounted thereto.

[Balloon Mounting Jig]

Figure 3:
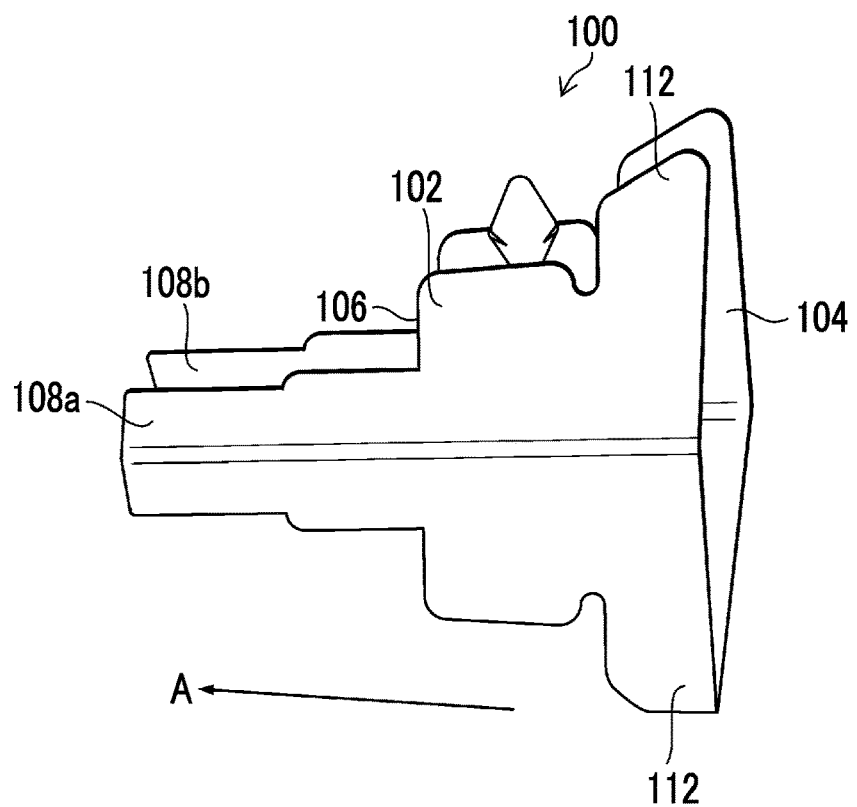
FIG. 3 is a plan view of a balloon mounting jig.
Figure 4:
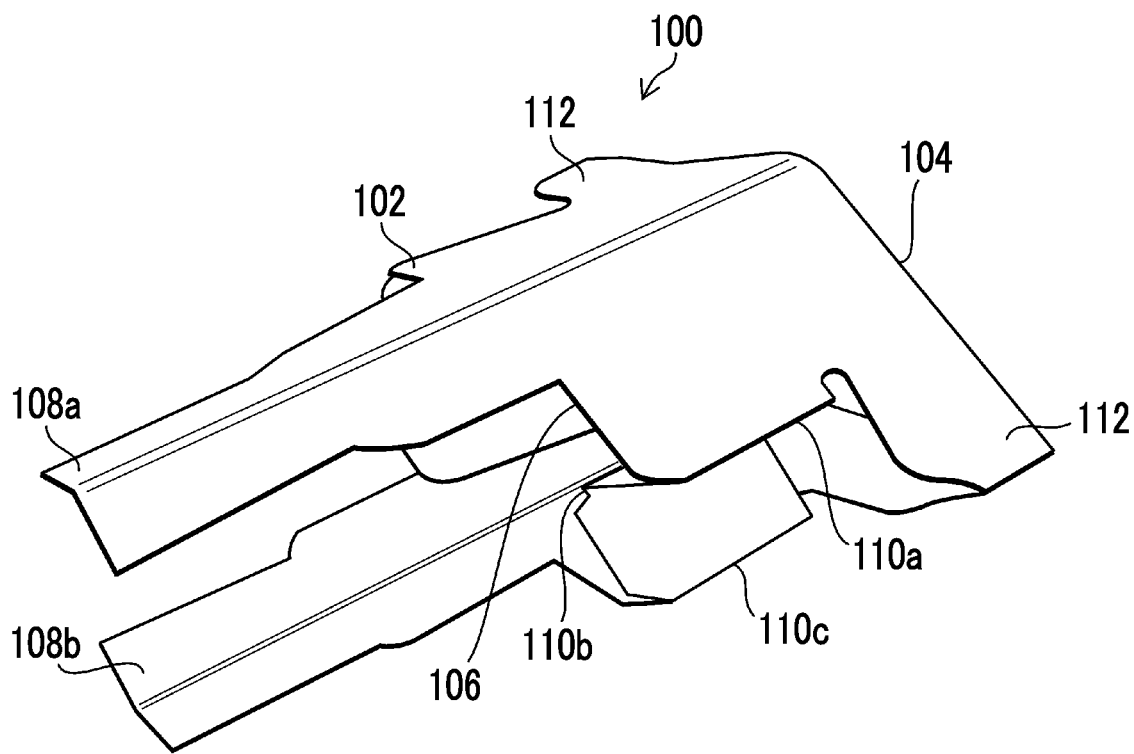
FIG. 4 is a perspective view showing a main body in a state where a first opening part and a second opening part are opened.
Figure 5:
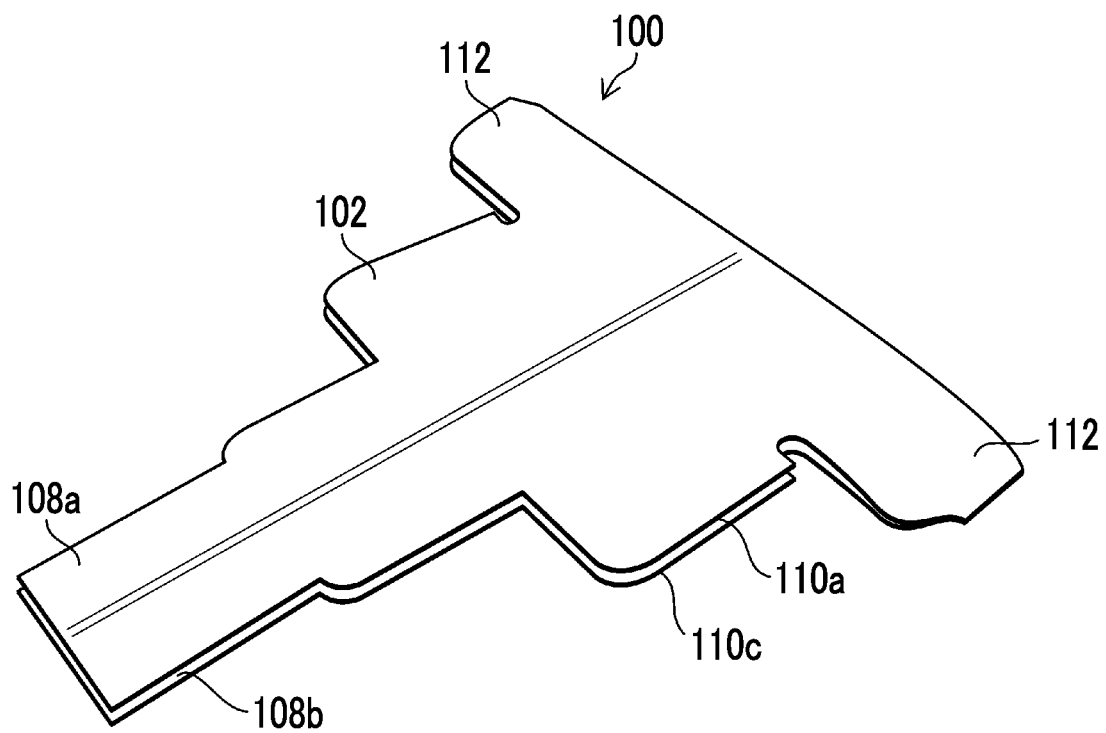
FIG. 5 is a perspective view showing the main body in a state where the main body is folded.

Next, the balloon mounting jig according to the present embodiment will be described. FIG. 3 is a plan view of the balloon mounting jig. FIG. 4 is a perspective view in a state where a first opening part and a second opening part of the main body are opened. FIG. 5 is a perspective view of a state where the main body is folded. FIG. 6 is a plan view of a sheet for constituting the balloon mounting jig. A plan view VIA shown in FIG. 6 is a view seen from a side that is an inner surface in a case where the balloon mounting jig is assembled, and a plan view VIB is a view seen from the outer surface side. The balloon mounting jig is used for easily mounting the balloon 60 to the insertion part 12 of the endoscope 10. In the following, the embodiment in which the balloon 60 is mounted to the insertion part 12 will be described, but the target to which the balloon 60 is mounted is not limited to the insertion part 12. It is also possible that the balloon 60 is mounted to an insertion assisting tool (not shown) used as an aid in a case where the insertion part 12 is inserted into a body cavity.

The balloon mounting jig 100 has a main body 102 that is formed in a hollow cylindrical shape having a first opening part 104 at one end thereof and a second opening part 106 at the other end thereof. The second opening part 106 of the main body 102 has a pair of guide pieces 108a and 108b that face each other with the second opening part 106 interposed therebetween. Further, the main body 102 is formed with two sets of bent parts 110a, 110b, and 110c that are provided from one end thereof to the other end thereof and allow the main body 102 to be bent inward in both directions. The main body 102 can be bent inward by folding the bent parts 110a and 110c in a mountain form and folding the bent part 110b in a valley form. In addition, the main body 102 can be folded flat by being bent at the bent parts 110a, 110b, and 110c, and the pair of guide pieces 108a and 108b can be superimposed as shown in FIG. 5.

The pair of guide pieces 108a and 108b are provided so as to extend from the second opening part 106 toward a distal end side opposite to the side of the first opening part 104. The width of the pair of guide pieces 108a and 108b is formed to have a width narrower than that of the main body 102 that is folded flat. Thus, in a case where the balloon mounting jig 100 is mounted to the balloon 60, it is possible to dispose the pair of guide pieces 108a and 108b inside the first sleeve part 60A and the second sleeve part 60B of the balloon 60. In a case where the insertion part 12 of the endoscope 10 is mounted to the balloon 60, the insertion part 12 is inserted along the pair of guide pieces 108a and 108b, so that the insertion part 12 can be easily inserted into the first sleeve part 60A and the second sleeve part 60B.

On the first opening part 104 of the main body 102, there is provided a wing part 112 that extends from the main body 102 in a width direction and has a width larger than that of the main body 102 that is folded flat. The wing part 112 is a portion that is in contact with a recess part 310 (see FIG. 8) in a case where the wing part 112 is contained in a container 300 (see FIG. 8), which will be described later. As the wing part 112 is in contact with the recess part, movement and rotation of the main body 102 are prevented.

Such a balloon mounting jig 100 can be formed by using, for example, a sheet S shown in FIG. 6. The bent parts 110a and 110c formed on the main body 102 of the sheet S are folded in a mountain form, the bent part 110b is folded in a valley form, the bent part 110d provided on the wing part 112 is folded in half in a mountain form, and the insertion piece 116 provided on the main body 102 is inserted into a hole part 118 provided at an end part of the opposite side of the main body 102. Accordingly, the balloon mounting jig 100 in which the main body 102 is formed in a hollow cylindrical shape can be formed.

It is preferable that the main body 102 and the pair of guide pieces 108a and 108b are made of a material that does not easily adhere to a rubber product such as silicone rubber or latex which is a balloon material, and specifically, paper such as drawing paper or Kent paper, or resin such as fluorine resin, silicone resin, polypropylene resin, or polycarbonate resin can be used. Further, in a case where the main body 102 and the pair of guide pieces 108a and 108b are made of paper, it is preferable that YUPO paper (registered trademark) that can easily expand and fold the main body 102 and is not easily torn is used.

(Surface Property of Balloon Mounting Jig)

In the balloon mounting jig 100 of the present embodiment, as shown in the plan view VIA of FIG. 6, a sliding surface 120 on which the outer peripheral surface of the insertion part 12 of the endoscope 10 is slidable is formed on the inner surfaces of the main body 102 and the pair of guide pieces 108a and 108b. That is, the sliding surface 120 has sliding property with respect to the insertion part 12 of the endoscope 10.

It is preferable that the sliding surface 120 is provided in a region where at least the insertion part 12 is in contact with the main body 102 and the pair of guide pieces 108a and 108b, in a case where the insertion part 12 is inserted, among the inner surfaces of the main body 102 and the pair of guide pieces 108a and 108b of the balloon mounting jig 100. It is more preferable that, in a case where the balloon mounting jig is assembled, the sliding surface 120 is provided in the entire region of a first surface 102a which is the same surface as the guide piece 108a, a second surface 102b which is the same surface as the guide piece 108b, and the pair of guide pieces 108a and 108b. It is still more preferable that the sliding surface 120 is provided in the entire region of the inner surface of the main body 102 including the first surface 102a, the second surface 102b, and side surfaces 102c and 102d provided between the first surface 102a and the second surface 102b and the inner surfaces of the pair of guide pieces 108a and 108b. In the plan view VIA shown in FIG. 6, the sliding surface 120 is provided in the entire region of the first surface 102a which is the same surface as the guide piece 108a, the second surface 102b which is the same surface as the guide piece 108b, and the pair of guide pieces 108a and 108b.

As a method of providing the sliding surface 120 on the inner surfaces of the main body 102 and the pair of guide pieces 108a and 108b, the method can be performed by making the surface a wrinkled uneven surface or providing a coating layer made of a plastic material.

For example, (1) roughening the inner surface by filing, (2) blasting treatment by injecting spherical or acute-angled granules formed of resin or the like, (3) thermal transfer to a die having a rough surface and unevenness, and (4) formation of a plurality of streak shapes by microfabrication are used to make the surface a wrinkled uneven surface. The coating layer made of the plastic material can be formed by applying a fluorine or silicon-based coating material. In a case where the streak shape is formed by microfabrication and the roughness of the coating layer has directionality, by having the same directionality as an insertion direction of the insertion part 12, the insertion part 12 can be slidable in the insertion direction.

In a case where the material of the balloon mounting jig 100 is paper, the insertion part 12 is sufficiently slidable with respect to the balloon mounting jig 100, and thus the inner surface of the main body 102 can be the sliding surface 120 without treating the inner surface.

By forming the inner surfaces of the main body 102 and the pair of guide pieces 108a and 108b as the sliding surface 120, the movement (sliding) of the insertion part 12 such as insertion or removal of the insertion part 12 to the balloon mounting jig 100 can be smoothly performed even in a state where the tension of the balloon 60 is applied from around the pair of guide pieces 108a and 108b.

As shown in the plan view VIB of FIG. 6, the outer surfaces of the pair of guide pieces 108a and 108b have a high friction part 122 provided on a second opening part 106 side and a low friction part 124 provided on a distal end side of the high friction part 122 and having a smaller friction coefficient than the high friction part 122.

The high friction part 122 is formed by attaching a thin polypropylene sheet, applying a pressure-sensitive adhesive (tack property) coating such as low hardness silicon, or attaching smooth paper such as laminated paper or YUPO paper. Further, the low friction part 124 can be formed by using the same method as the sliding surface 120 formed on the inner surface of the balloon mounting jig 100 described above.

By forming the outer surfaces of the pair of guide pieces 108a and 108b as regions having different friction coefficients of the high friction part 122 and the low friction part 124, it is possible that the balloon 60 is easy to slide at the low friction part 124, and thus the balloon mounting jig 100 can be inserted into or removed from the first sleeve part 60A of the balloon 60. Further, it is possible that the balloon 60 is hard to slide at the high friction part 122, and thus the balloon mounting jig 100 can be moved integrally with the second sleeve part 60B of the balloon 60.

As long as the high friction part 122 and the low friction part 124 have the above-mentioned effects, it is possible to form two regions having relatively different friction coefficients by forming only one of high friction part 122 and low friction part 124. For example, in a case where the balloon mounting jig 100 is made of resin, since a resin surface has a large frictional resistance, it is possible to form the high friction part 122 and the low friction part 124 on the outer surfaces of the pair of guide pieces 108a and 108b by performing a process (process of forming the sliding surface 120) of forming the above-mentioned low friction part 124 without performing the process of forming the high friction part 122. Further, in a case where the balloon mounting jig 100 is made of paper, since the balloon mounting jig 100 made of the paper has a small frictional resistance, it is possible to form the high friction part 122 and the low friction part 124 on the outer surfaces of the pair of guide pieces 108a and 108b by performing a process of forming the above-mentioned high friction part 122 without performing the process of forming the low friction part 124.

In this way, because of the friction coefficient of the material itself constituting the balloon mounting jig 100, it is possible to form the high friction part 122 and low friction part 124 having different friction coefficients on the outer surfaces of the pair of the guide pieces 108a and 108b by forming either the high friction part 122 or the low friction part 124.

(Shape of One Pair of Guide Pieces)

Next, a shape of the pair of guide pieces 108a and 108b will be described. As shown in FIGS. 3 to 6, the pair of guide pieces 108a and 108b have a narrow part 126 provided on the distal end side and a wide part 128 provided on the second opening part 106 side. The wide part 128 is formed to be wider than the narrow part 126.

In the wide part 128, it is preferable that a total length of the widths of the pair of guide pieces 108a and 108b is equal to or less than the length of the outer periphery of the insertion part 12 of the endoscope 10 to be inserted. By setting the total length of the widths of the pair of guide pieces 108a and 108b to be equal to or less than the outer periphery of the insertion part 12, it is possible to prevent the wide part 128 disposed around the insertion part 12 from overlapping and becoming thick in a case where the insertion part 12 is inserted from the first opening part 104 along the pair of guide pieces 108a and 108b.

Further, as the total length of the width of the wide part 128 becomes equal to the outer periphery of the insertion part 12, the insertion part 12 has a smaller region in direct contact with the balloon 60. Therefore, the insertion part 12 can be easily moved with respect to the balloon mounting jig 100 while the balloon mounting jig 100 is inserted into the balloon 60.

The narrow part 126 provided at the distal end of the pair of guide pieces 108a and 108b is formed to be narrower than the wide part 128. In a state where the insertion part 12 is inserted into the balloon mounting jig 100, a part of the insertion part 12 is in direct contact with the balloon 60, and the other part is in contact with the balloon 60 via the narrow part 126. As a result, the balloon mounting jig 100 is pulled out by holding the portion where the balloon 60 disposed at the distal end of the insertion part 12 is in direct contact with the insertion part 12, so that the balloon mounting jig 100 can be extracted without moving the balloon 60.

It is preferable that the distal end side of the pair of guide pieces 108a and 108b has a side portion parallel to the insertion direction of the insertion part 12 and has a distal end shape without a taper. By making the shape of the distal end side of the pair of guide pieces 108a and 108b such a configuration, it is possible to insert the distal end of the pair of guide pieces 108a and 108b up to the distal end of the first sleeve part 60A of the balloon 60. Therefore, the insertion part 12 of the endoscope 10 can be inserted up to the distal end of the first sleeve part 60A.

(Mounting Jig Mounted Balloon)

Next, a form in which the balloon 60 is mounted to the balloon mounting jig 100 will be described. The balloon mounting jig 100 of the present invention can also be used by being contained in a container to be described later in a form in which the balloon 60 is mounted. Hereinafter, the configuration in which the balloon 60 is mounted to the balloon mounting jig 100 is referred to as "mounting jig mounted balloon 200".

Figure 7:
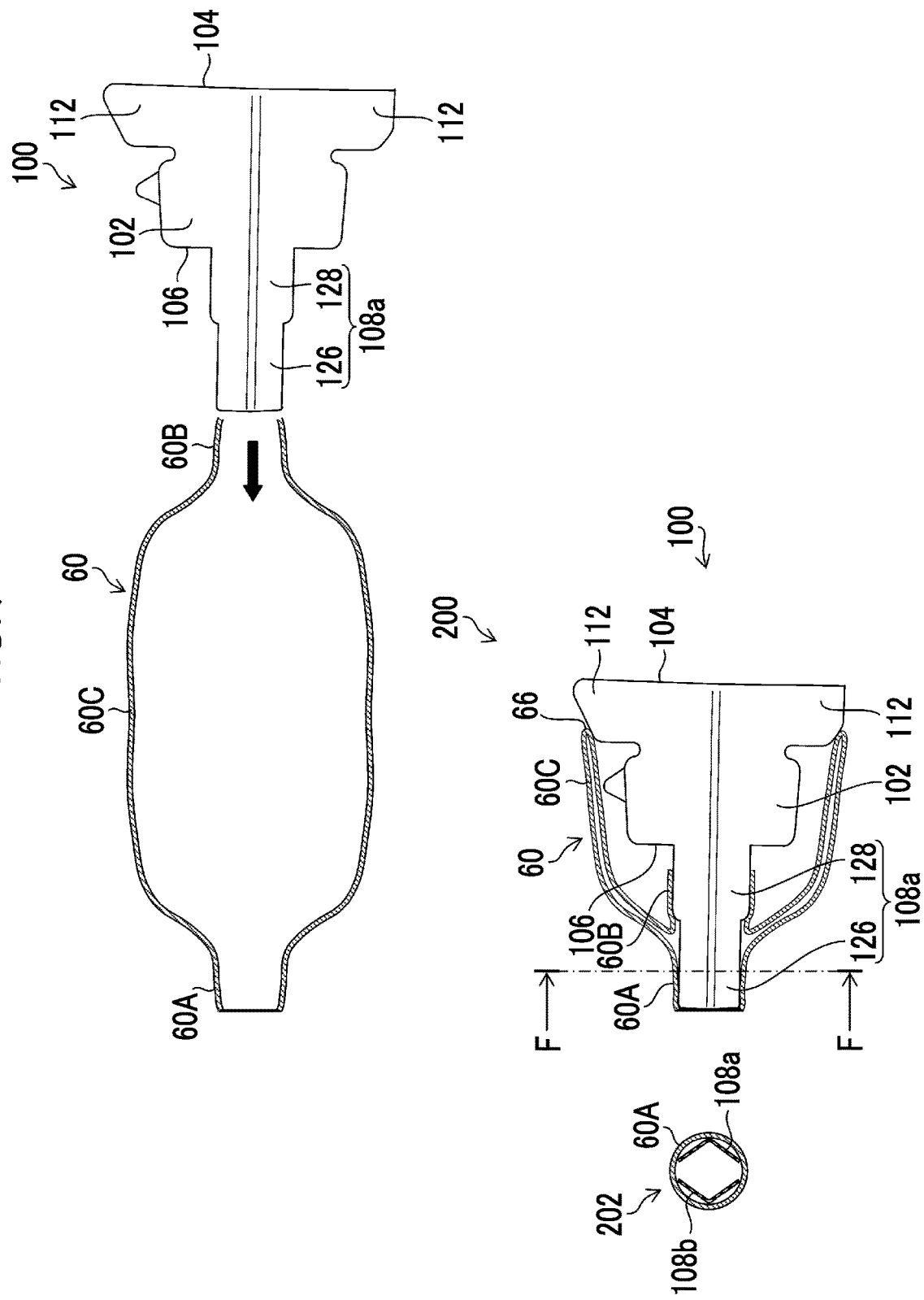
FIG. 7 is a diagram for explaining a form in which the balloon is mounted to the balloon mounting jig.

FIG. 7 is a diagram showing a form in which the balloon 60 is mounted to the balloon mounting jig 100. In a case where the balloon mounting jig 100 is mounted to the balloon 60, first, the pair of guide pieces 108a and 108b are inserted into the second sleeve part 60B, and a portion of the distal end side of the pair of guide pieces 108a and 108b is protruded from the second sleeve part 60B. Further, by inserting the pair of guide pieces 108a and 108b inside the balloon main body 60C, the second sleeve part 60B moves to the first sleeve part 60A side, and the balloon main body 60C is folded back inside, so that a folded opening part 66 is formed. Further, by inserting the guide pieces 108a and 108b and the main body 102 from the folded opening part 66, the portion (the narrow part 126) of the distal end side of the guide pieces 108a and 108b protruding from the second sleeve part 60B is inserted into the first sleeve part 60A, and the second sleeve part 60B is disposed to the wide part 128. Accordingly, the balloon mounting jig 100 can be mounted to the balloon 60.

As shown in FIG. 7, in a state where the balloon 60 is mounted to the balloon mounting jig 100, the second sleeve part 60B is disposed inside the folded opening part 66. In the pair of guide pieces 108a and 108b, the narrow part 126 of the guide pieces 108a and 108b is disposed inside the first sleeve part 60A. Further, the wide part 128 of the guide pieces 108a and 108b is disposed inside the second sleeve part 60B. The pair of guide pieces 108a and 108b in the first sleeve part 60A is disposed to be bent outward along a longitudinal direction A (see FIG. 3) of the pair of guide pieces 108a and 108b, as shown in an F-F cross section 202. Thus, in a state where the balloon mounting jig 100 is mounted to the balloon 60, the first opening part 104 can be slightly opened from the completely folded state. Accordingly, it is possible to easily insert the insertion part 12 of the endoscope 10 into the first opening part 104.

In the mounting jig mounted balloon 200, the first sleeve part 60A is disposed at the narrow part 126 provided on the distal end side of the pair of guide pieces 108a and 108b. Therefore, it is preferable that the low friction part 124 is provided on the outer surface of the narrow part 126 of the pair of guide pieces 108a and 108b. In a case where the insertion part 12 of the endoscope 10 is inserted into the mounting jig mounted balloon 200, the insertion part 12 is inserted up to the distal end of the pair of guide pieces 108a and 108b, and the first sleeve part 60A of the balloon 60 is disposed at the distal end of the insertion part 12. The first sleeve part 60A can be mounted to the distal end of the insertion part 12 by pulling out the balloon mounting jig 100 without moving the position of the first sleeve part 60A with respect to the insertion part 12. In this case, by forming the outer surface of the narrow part 126 in which the first sleeve part 60A is disposed as the low friction part 124, it is possible to easily extract the pair of guide pieces 108a and 108b from the first sleeve part 60A.

Further, in the mounting jig mounted balloon 200, the second sleeve part 60B is disposed at the wide part 128 provided on a proximal end side of the pair of guide pieces 108a and 108b. Therefore, it is preferable that the high friction part 122 is provided on the outer surface of the wide part 128 of the pair of guide pieces 108a and 108b. Since the second sleeve part 60B is moved to the proximal end side of the insertion part 12 after the insertion part 12 is inserted, it is possible that the second sleeve part 60B and the balloon mounting jig 100 can be moved integrally without the second sleeve part 60B sliding on the pair of guide pieces 108a and 108b by forming the wide part 128 in which the second sleeve part 60B is disposed as the high friction part 122. Since the inner surfaces of the pair of guide pieces 108a and 108b and the main body 102 have a sliding surface on which the outer peripheral surface of the insertion part 12 is slidable, the balloon mounting jig 100 is configured to be easily moved on the insertion part 12. Further, since the wide part 128 has a wider width than the narrow part 126, an area where the insertion part 12 and the second sleeve part 60B are in contact with each other can be reduced, the influence of the tension of the second sleeve part 60B is reduced, and the balloon mounting jig 100 is easily moved on the insertion part 12.

In the mounting jig mounted balloon 200, the insertion part 12 may be inserted and the balloon 60 may be mounted in this state. The mounting jig mounted balloon 200 may be contained in the container 300 shown in FIG. 8, and the insertion part 12 may be inserted and the balloon 60 may be mounted to the insertion part 12 while being contained in the container 300. Hereinafter, the container 300 will be described.

(Container)

Figure 8:
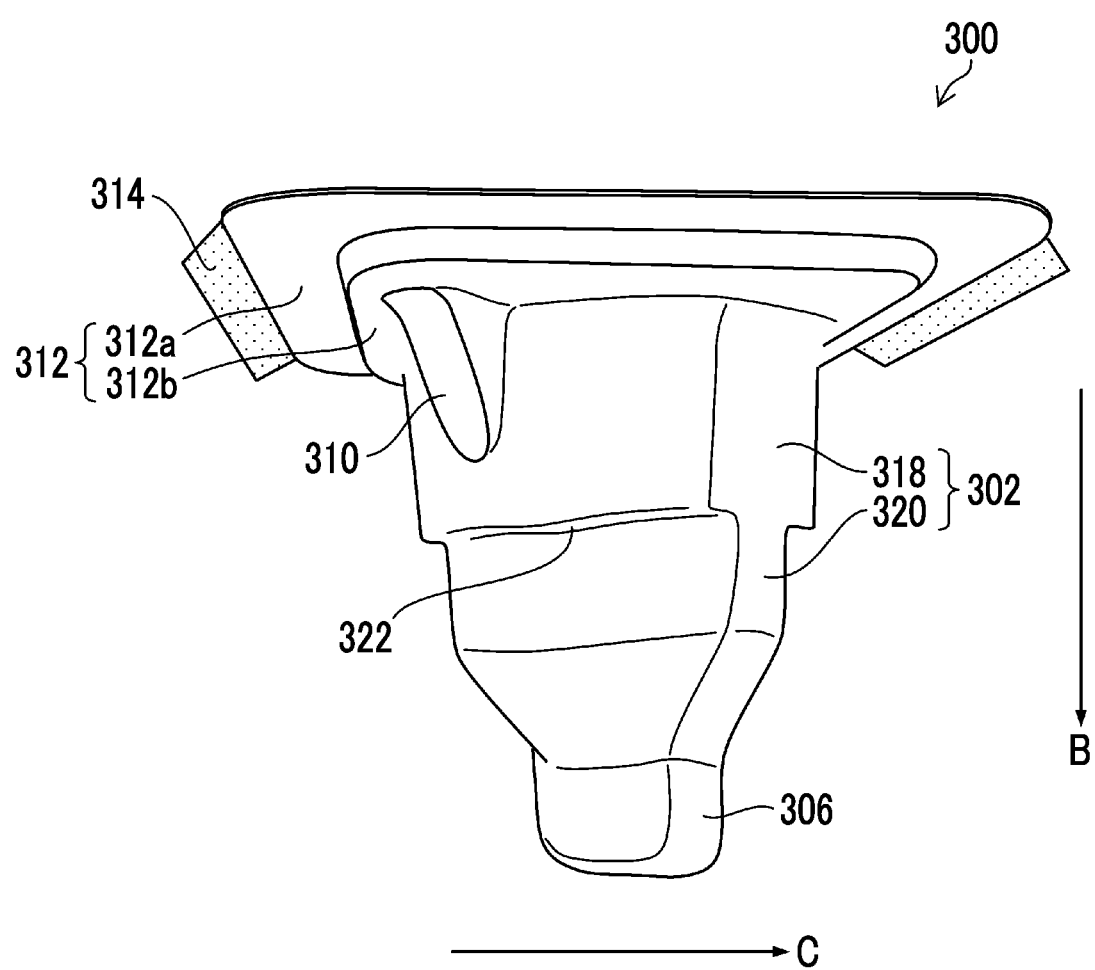
FIG. 8 is a perspective view showing a container.
Figure 9:
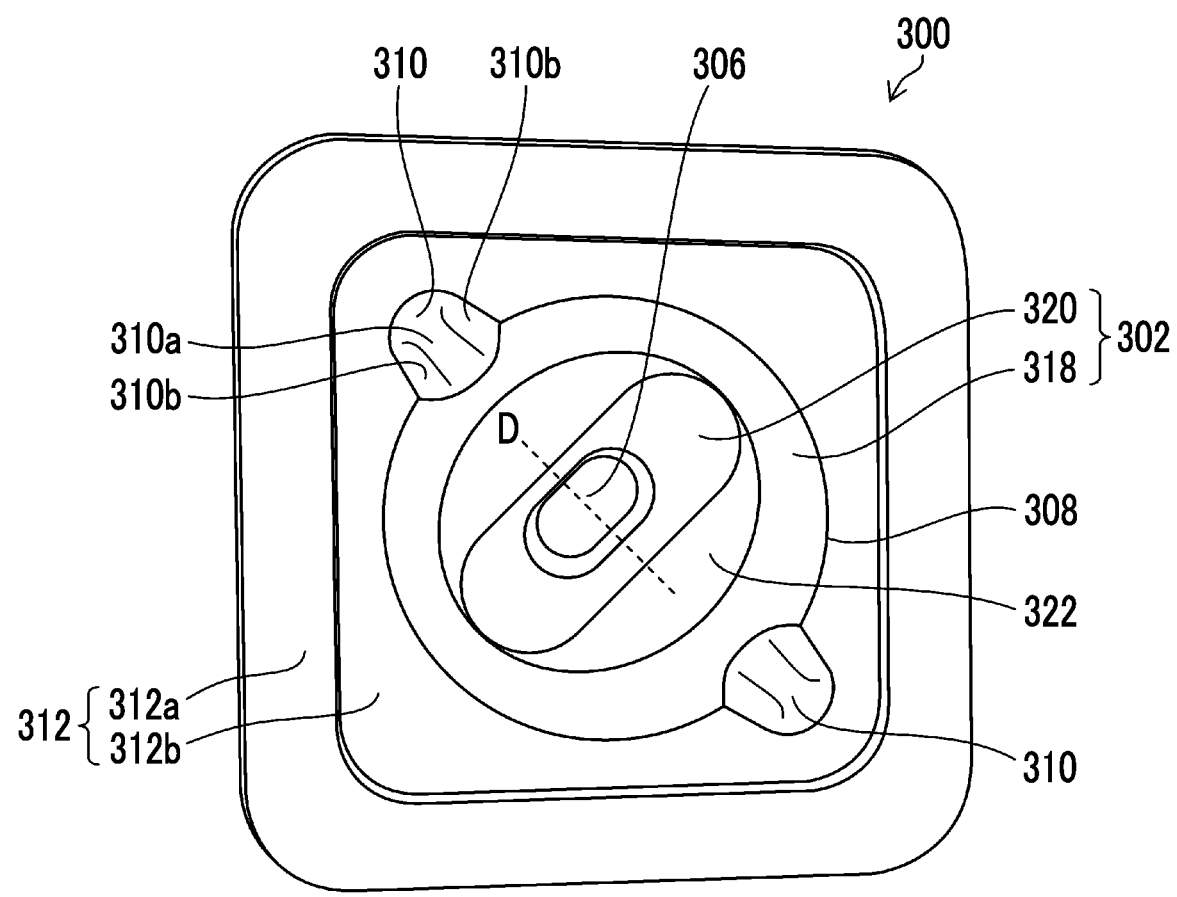
FIG. 9 is a plan view showing the container with a lid part removed.
Figure 10:
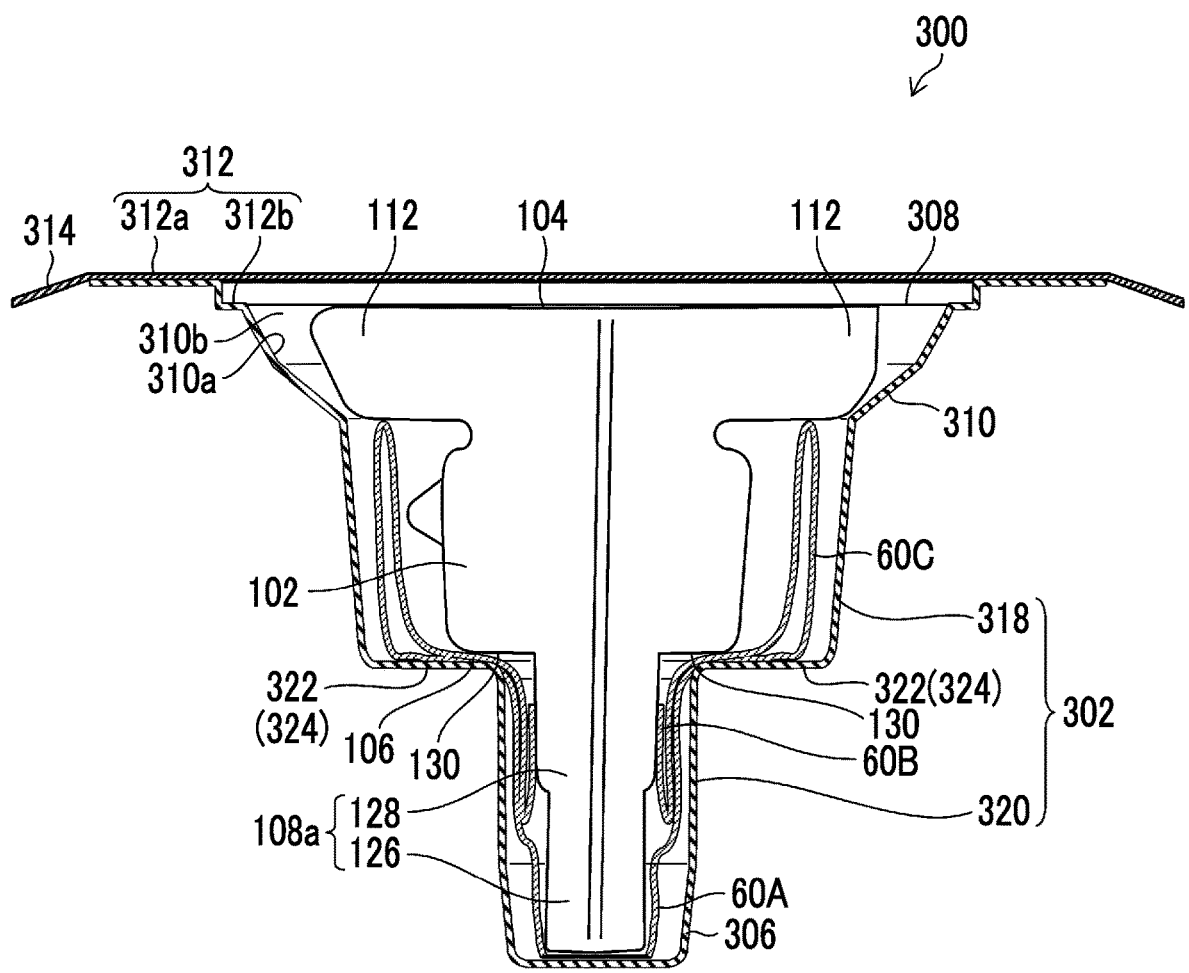
FIG. 10 is a cross-sectional view showing a state where the mounting jig mounted balloon is contained.

FIG. 8 is a perspective view showing the container. FIG. 9 is a plan view showing the container with a lid part removed. FIG. 10 is a cross-sectional view showing a state where the balloon mounting jig in which the balloon is mounted is contained in the container.

The container 300 has a trunk 302 including a tubular trunk main body 318 and a middle groove part 320 narrower than the trunk main body 318, a small groove part 306 provided on the middle groove part 320 side of the trunk 302, and a container opening part 308 provided on the opposite side of the small groove part 306. Between the trunk main body 318 and the middle groove part 320, a stepped part 322 provided with a surface in a direction perpendicular to an insertion direction B of the balloon mounting jig 100 is provided. On the side of the container opening part 308 of the trunk 302, a recess part 310 formed in a concave shape in a direction perpendicular to the insertion direction B of the balloon mounting jig 100 is provided. Further, the container opening part 308 has a flange part 312 that extends from the container opening part 308 in a direction perpendicular to the insertion direction B of the balloon mounting jig 100, and a lid part 314 is attached to the flange part 312.

In a case where the mounting jig mounted balloon 200 is contained, the balloon main body 60C and the second sleeve part 60B of the balloon 60 are contained in the trunk 302, and the first sleeve part 60A is contained in the small groove part 306. Further, in the trunk 302, a part of the balloon main body 60C and the second sleeve part 60B are contained in the middle groove part 320, and the other part of the balloon main body 60C is contained in the trunk main body 318. By containing the balloon main body 60C in the trunk 302, it is possible to prevent the balloon main bodies 60C disposed around the balloon mounting jig 100 from sticking to each other, to thereby maintain the shape of the balloon main body 60C.

Further, in the balloon mounting jig 100, the main body 102 is contained in the trunk main body 318 of the trunk 302, and the pair of guide pieces 108a and 108b are contained in the small groove part 306 and the middle groove part 320. By containing the balloon mounting jig 100 in the container 300 in this way, the end parts of the main body 102 of the balloon mounting jig 100 on the side of the pair of guide pieces 108a and 108b are disposed at the boundary between the trunk main body 318 and the middle groove part 320. That is, the stepped part 322 of the container 300 can be flush with the end part of the main body 102 of the balloon mounting jig 100 on the side of the pair of guide pieces 108a and 108b in a direction perpendicular to the insertion direction (the insertion direction B of the balloon mounting jig 100) of the insertion part 12 of the endoscope 10. With this configuration, the stepped part 322 is a second restricting surface 324 that restricts the position of the main body 102 of the balloon mounting jig 100 in the insertion direction, and the second restricting surface 324 and the end part of the main body 102 of the balloon mounting jig 100 on the side of the pair of guide pieces 108a and 108b which is a restricted part 130 are in contact with each other, so that the position of the balloon mounting jig 100 in the insertion direction can be restricted.

It is preferable that the trunk main body 318 is formed in a taper shape in which an inner diameter becomes larger from the middle groove part 320 toward the container opening part 308. By forming the taper shape that expands toward the container opening part 308, it is possible to easily take out the mounting jig mounted balloon 200. Further, even in manufacturing the container 300, it is possible to easily extract the container 300 from a die by forming the container 300 to expand toward the container opening part 308.

The small groove part 306 contains the first sleeve part 60A and the narrow part 126 of the pair of guide pieces 108a and 108b. The small groove part 306 has an elliptical sectional shape cut in a direction C perpendicular to an axis direction of the trunk 302 (the same direction as the insertion direction B of the balloon mounting jig 100) (see FIG. 9). In a state where the mounting jig mounted balloon 200 is contained in the container 300, the distal end of the pair of guide pieces 108a and 108b is preferably disposed along a short axis direction D of the elliptical shape of the small groove part 306. "The guide pieces are disposed along the short axis direction" means that the pair of guide pieces are respectively disposed on both sides centering around the short axis of the small groove part 306.

In the recess part 310, the wing part 112 of the balloon mounting jig 100 is contained. The recess part 310 has a positioning surface 310a that is formed in a direction perpendicular to the insertion direction B of the balloon mounting jig 100, and a first restricting surface 310b that is formed in a circumferential direction of the trunk. In a case where the positioning surface 310a and the wing part 112 of the balloon mounting jig 100 are in contact with each other, a position in the direction perpendicular to the insertion direction B of the balloon mounting jig 100 is determined, and thus, it is possible to prevent the balloon main body 60C from contacting the side surface of the trunk 302, to thereby stabilize the form of the balloon.

Further, similarly, the first restricting surface 310b is in contact with the wing part 112 to restrict a rotation direction with respect to a central axis in the insertion direction B of the balloon mounting jig 100. Thus, it is possible to prevent rotation of the mounting jig mounted balloon 200 due to transportation, to prevent the balloon main bodies 60C disposed around the balloon mounting jig 100 from sticking to each other, and to retain the form of the balloon main body 60C.

The flange part 312 is formed to expand from the container opening part 308 in a direction perpendicular to the insertion direction B of the balloon mounting jig 100. The flange part 312 is configured by an outer peripheral part 312a and an inner peripheral part 312b, and is provided in the order of the inner peripheral part 312b and the outer peripheral part 312a from the container opening part 308. The inner peripheral part 312b is formed closer to the middle groove part 320 than the outer peripheral part 312a in the insertion direction B of the balloon mounting jig 100. That is, the outer peripheral part 312a and the inner peripheral part 312b are formed in a stepped shape, and the outer peripheral part 312a is formed to protrude in a direction opposite to the side of the middle groove part 320.

The lid part 314 is attached to the flange part 312, and seals the inside of the container 300 to ensure sterility. The lid part 314 is attached to an affix target surface provided on a proximal end side of the outer peripheral part 312a of the flange part 312. By attaching the lid part 314 to the outer peripheral part 312a, it is possible to make an area where the lid part 314 is attached small.

[Balloon Mounting Method]

Next, using FIGS. 11 to 17, a balloon mounting method using a package in which the balloon mounting jig to which the balloon 60 is mounted is contained in the container (hereinafter, also referred to as "package of mounting jig mounted balloon") will be described.

Figure 11:
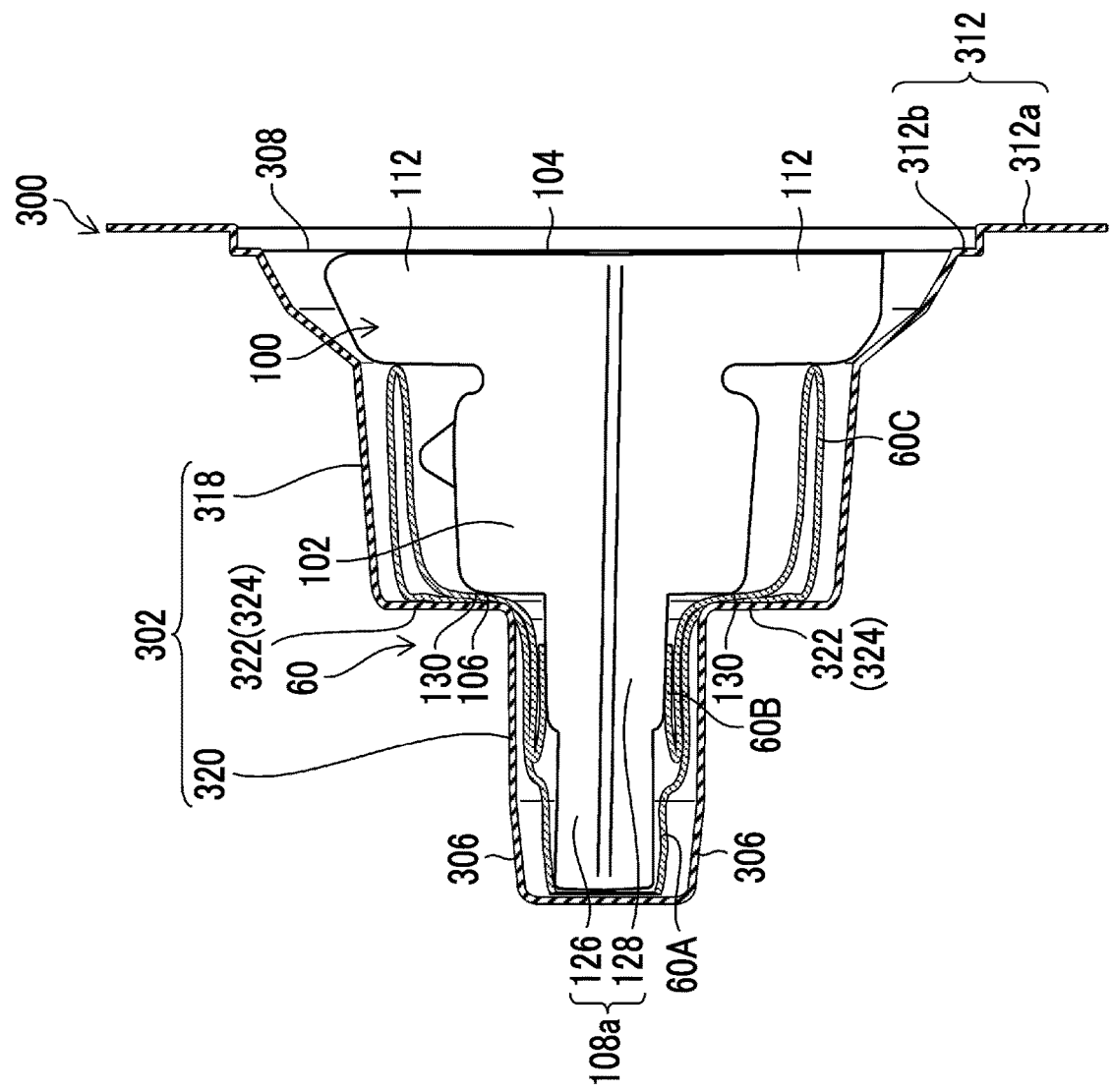
FIG. 11 is a diagram for explaining a method for mounting the balloon in the insertion part.
Figure 12:
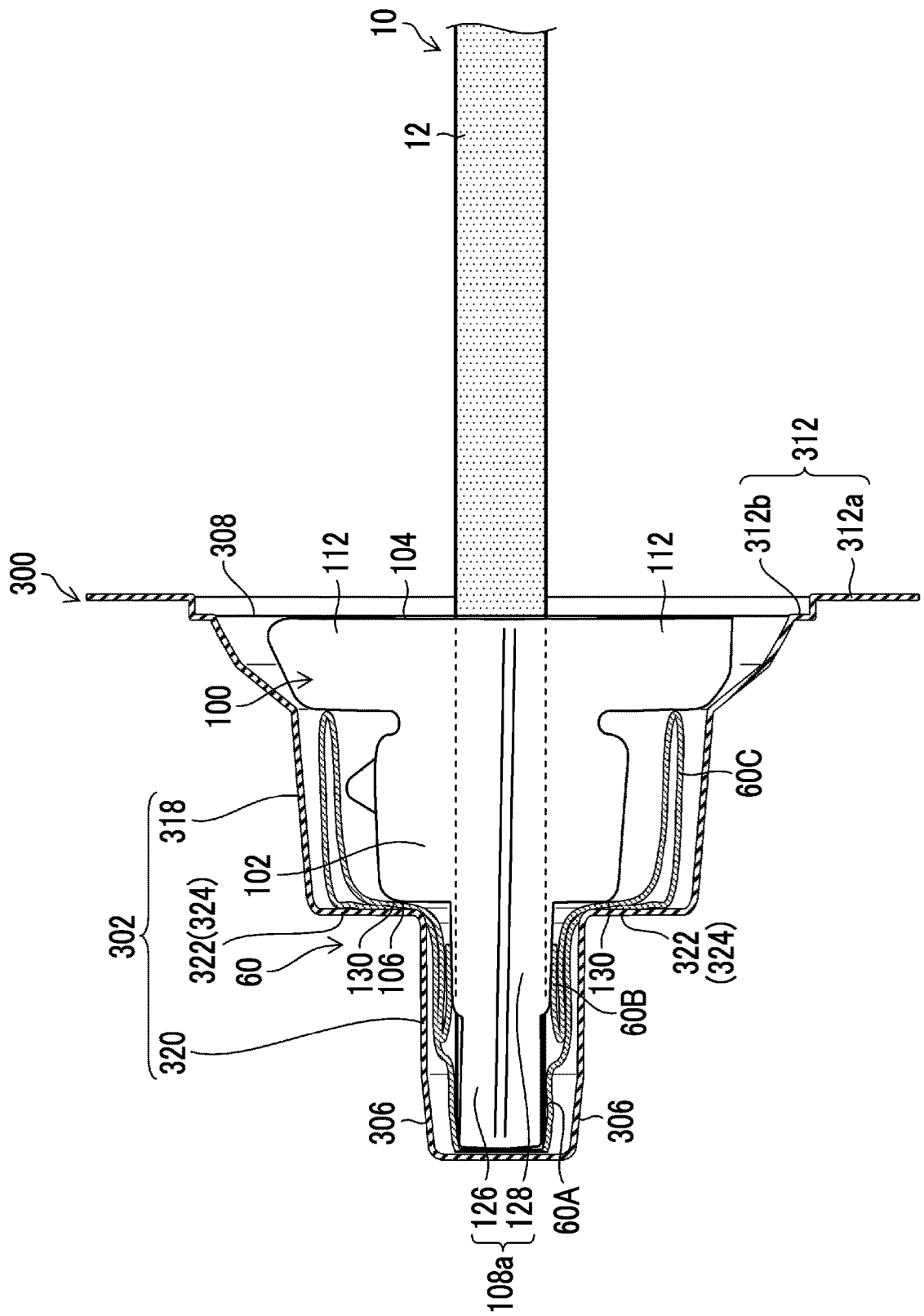
FIG. 12 is a diagram for explaining a method for mounting the balloon in the insertion part.

The package of the mounting jig mounted balloon is prepared, and the lid part 314 is removed. FIG. 11 is a diagram showing a state where the insertion part of the endoscope is inserted into the package of the mounting jig mounted balloon from which the lid part is removed. As shown in FIG. 12, the package of the mounting jig mounted balloon from which the lid part 314 is removed is disposed so that the side of the first opening part 104 of the balloon mounting jig 100 is disposed on the side of the container opening part 308 of the container 300. In this state, the insertion part 12 of the endoscope 10 is inserted from the first opening part 104. The insertion part 12 is inserted until the insertion part 12 runs into the small groove part 306 of the container 300.

The inner surfaces of the main body 102 and the pair of guide pieces 108a and 108b of the balloon mounting jig 100 have a sliding surface 120 on which the outer peripheral surface of the insertion part 12 is slidable. Therefore, the insertion part 12 can be easily inserted into the balloon mounting jig 100.

FIG. 12 is a diagram for explaining a state where the insertion part is inserted until a distal end of the insertion part runs into a distal end of the small groove part. The insertion part 12 inserted from the first opening part 104 passes through the inside of the main body 102, and is inserted from the second opening part 106 between the pair of guide pieces 108a and 108b. As shown in FIG. 6, in the mounting jig mounted balloon 200, the first sleeve part 60A and the second sleeve part 60B are disposed outside the pair of guide pieces 108a and 108b. Accordingly, by inserting the insertion part 12 between the pair of guide pieces 108a and 108b, it is possible to insert the insertion part 12 into the first sleeve part 60A and the second sleeve part 60B through the pair of guide pieces 108a and 108b.

In the mounting jig mounted balloon 200, it is preferable that the distal end of the pair of guide pieces 108a and 108b is contained in the container 300 in a state of protruding from the distal end of the first sleeve part 60A by 0.5 to 3 mm in consideration of such a dimension that the distal end of the insertion part 12 drags the balloon in mounting the balloon to protrude from the distal end. In a state where the pair of guide pieces 108a and 108b are in contact with the distal end of the small groove part 306, as the distal end of the insertion part 12 is inserted until the insertion part 12 runs into the distal end of the small groove part 306, it is possible to make the end part of the first sleeve part 60A and the distal end of the insertion part 12 match each other.

In a case where the insertion part 12 of the endoscope 10 is inserted along the pair of guide pieces 108a and 108b from the first opening part 104 of the balloon mounting jig 100, the insertion resistance is applied due to the influence of the tension of the first sleeve part 60A and the second sleeve part 60B of the balloon 60, and the balloon mounting jig 100 applies a force in the insertion direction of the insertion part 12. By contacting the stepped part 322 provided on the container 300 with the restricted part 130 of the balloon mounting jig 100, it is possible to prevent the balloon mounting jig 100 from moving in the insertion direction of the insertion part 12. Therefore, it is possible to prevent a force from being applied to the pair of guide pieces 108a and 108b in the insertion direction of the insertion part 12, and it is possible to prevent the pair of guide pieces 108a and 108b from bending. As a result, the insertion part 12 can be easily inserted up to the distal end of the first sleeve part 60A of the balloon 60.

Figure 13:
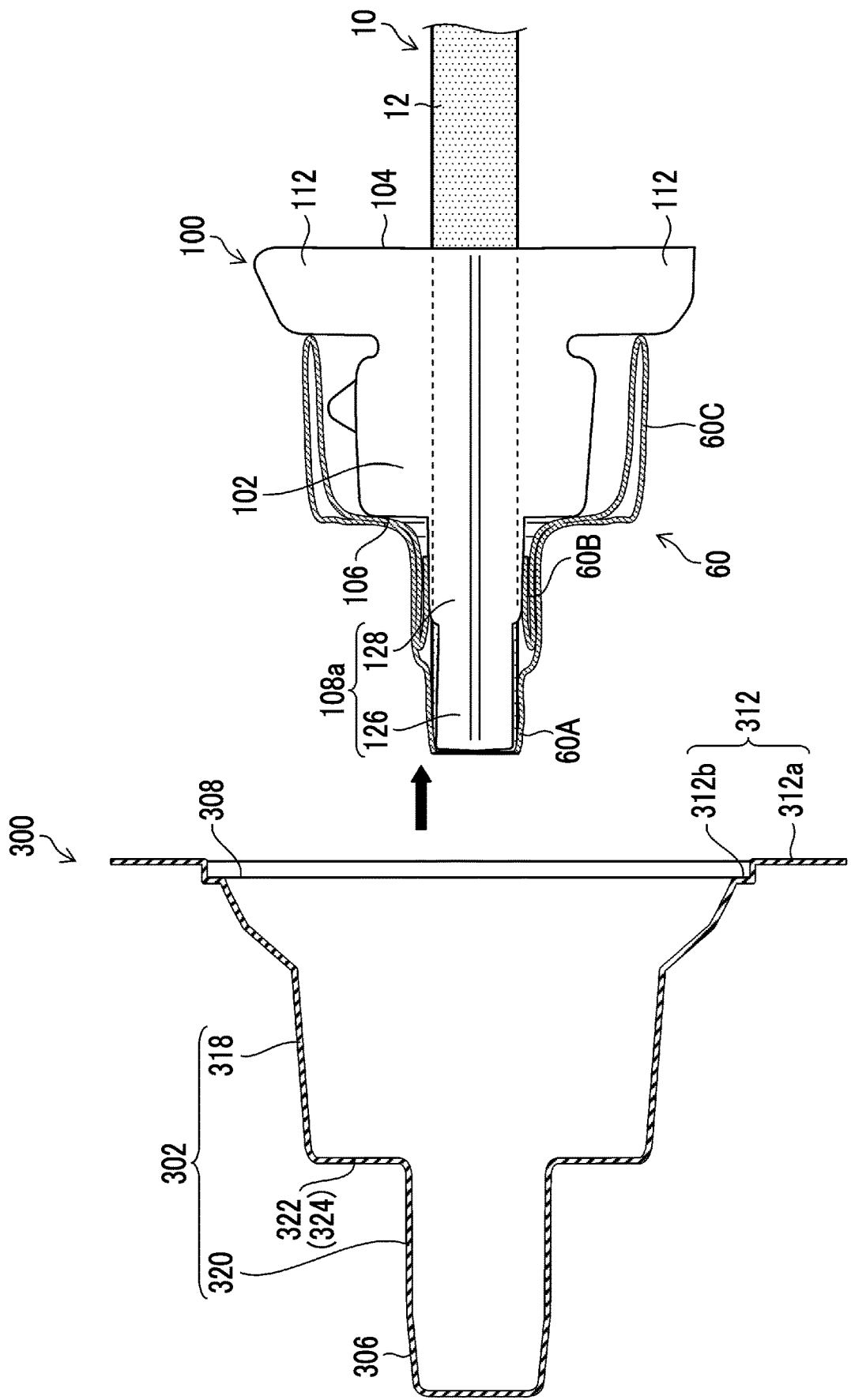
FIG. 13 is a diagram for explaining a method for mounting the balloon in the insertion part.

Next, as shown in FIG. 13, the mounting jig mounted balloon 200 into which the insertion part 12 is inserted is pulled out of the container 300. In the pulled-out mounting jig mounted balloon 200 and the endoscope 10, in a case where positions of the distal end of the insertion part 12 and the end part of the first sleeve part 60A of the balloon 60 do not match each other, the balloon mounting jig 100 is moved in the longitudinal axis direction of the insertion part 12 so that the positions of the distal end of the insertion part 12 and the end part of the first sleeve part 60A of the balloon 60 match each other. In pulling out the mounting jig mounted balloon 200 and the endoscope 10, and in a case where the positions of the distal end of the insertion part 12 and the end part of the first sleeve part 60A of the balloon 60 match each other, this process may not be performed.

Figure 14:
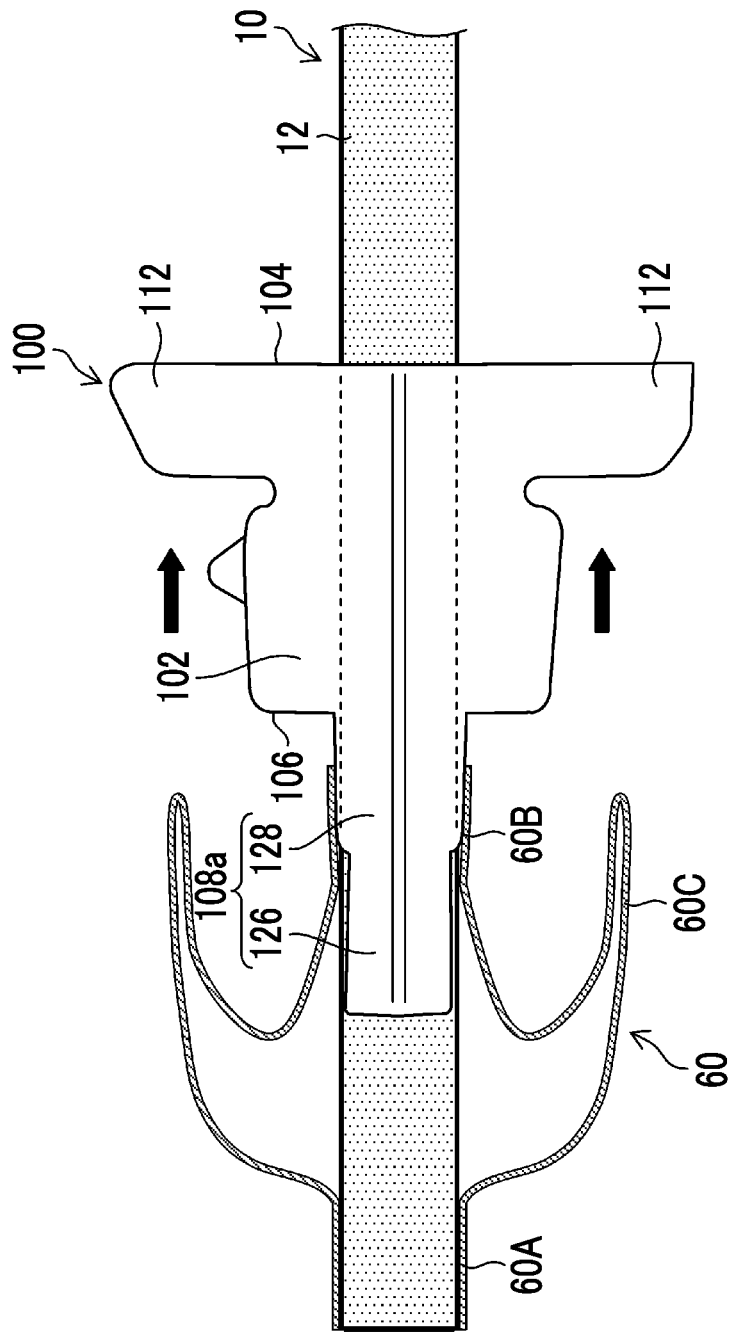
FIG. 14 is a diagram for explaining a method for mounting the balloon in the insertion part.
Figure 15:
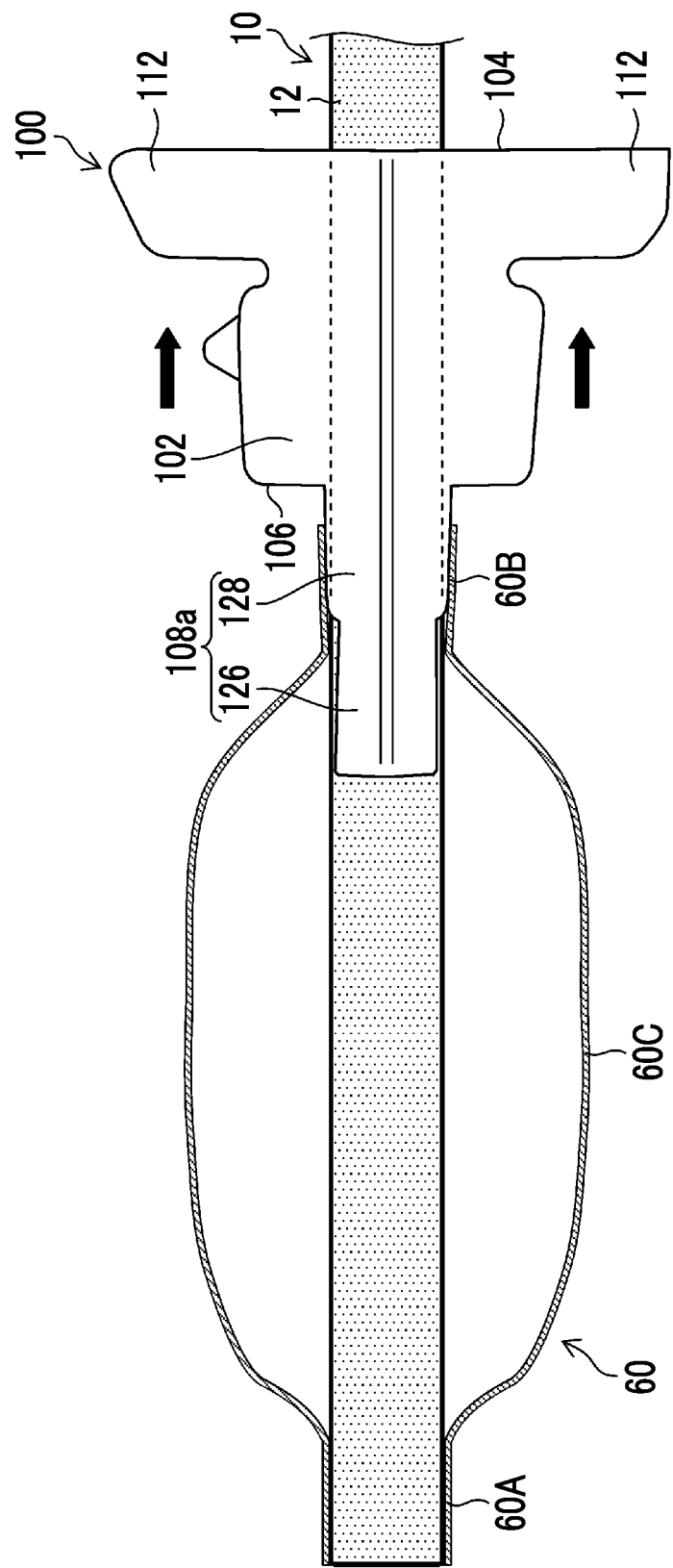
FIG. 15 is a diagram for explaining a method for mounting the balloon in the insertion part.

Next, a portion where the insertion part 12 and the first sleeve part 60A are in contact with each other is pressed. Specifically, the first sleeve part 60A is pressed against the insertion part 12 while avoiding the portion of the pair of guide pieces 108a and 108b of the insertion part 12. Further, in a state where the first sleeve part 60A is pressed, as shown in FIG. 14, the balloon mounting jig 100 is moved to the proximal end side of the insertion part 12. By moving the balloon mounting jig 100 in a state where the first sleeve part 60A is pressed, it is possible to fix the position of the first sleeve part 60A, and to move the position of the second sleeve part 60B together with the balloon mounting jig 100. As a result, as shown in FIG. 15, the second sleeve part 60B is brought out to the outside of the folded opening part 66.

In this case, since the outer surface of the pair of guide pieces 108a and 108b on the distal end side (the narrow part 126) is a low friction part 124 having a small friction coefficient, it is possible to easily extract only the pair of guide pieces 108a and 108b. Further, since the outer surface of the pair of guide pieces 108a and 108b on the second opening part 106 (the wide part 128) side is the high friction part 122, the second sleeve part 60B is hard to slide on the pair of guide pieces 108a and 108b. Therefore, in a state where the pair of guide pieces is pressed from above the second sleeve part 60B, the balloon 60 and the balloon mounting jig 100 are integrally moved toward the proximal end side of the insertion part 12 on the insertion part 12. Further, the second sleeve part 60B is disposed at the wide part 128, and the wide part 128 can increase a contact area between the pair of guide pieces 108a and 108b and the insertion part 12. Since the inner surfaces of the pair of guide pieces 108a and 108b have the sliding surface 120 as described above, the movement of the balloon mounting jig 100 on the insertion part 12 can be easily performed even in a state where the tension of the second sleeve part 60B is applied.

Figure 16:
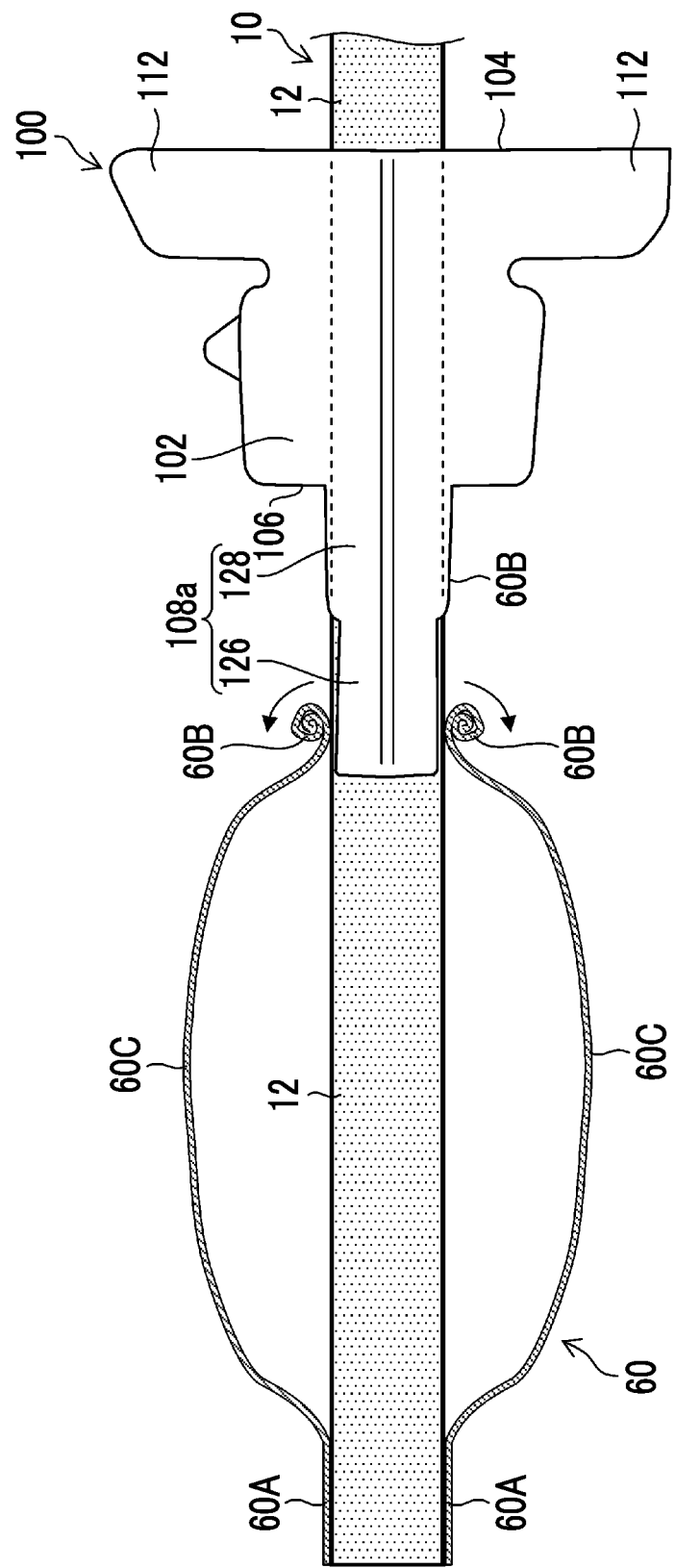
FIG. 16 is a diagram for explaining a method for mounting the balloon in the insertion part.

Next, as shown in FIG. 16, the second sleeve part 60B is wound toward the first sleeve part 60A until the pair of guide pieces 108a and 108b are removed while taking care so that the position of the balloon 60 is not moved. After winding the second sleeve part 60B until the pair of guide pieces 108a and 108b are removed, the balloon mounting jig 100 is removed. By moving the balloon mounting jig 100 to the insertion part 12 in a proximal end direction, the balloon mounting jig 100 is pulled out. In a case where the balloon mounting jig 100 is made of paper, the balloon mounting jig 100 may be broken and removed.

Figure 17:
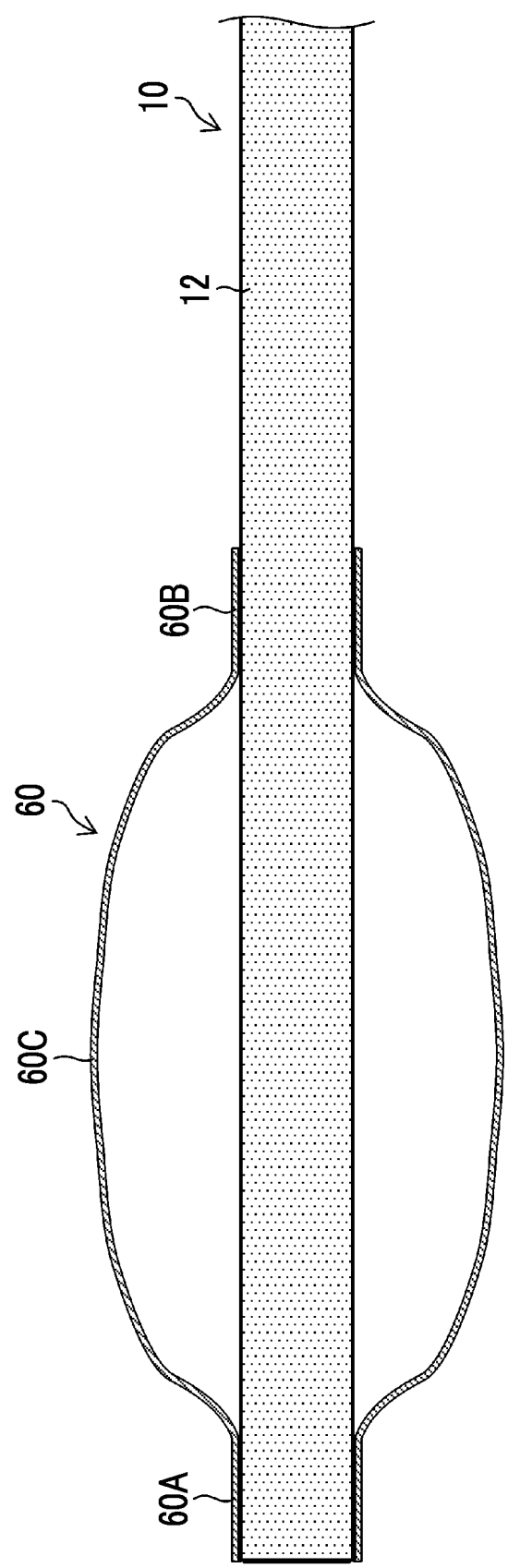
FIG. 17 is a diagram for explaining a method for mounting the balloon in the insertion part.

After removing the balloon mounting jig 100, the position of the balloon 60 is fixed so as not to move, and the second sleeve part 60B is rewound (FIG. 17). Finally, the balloon 60 is fixed to the insertion part 12 by fitting the first balloon fixing member 61 and the second balloon fixing member 62 into the first sleeve part 60A and the second sleeve part 60B of the balloon 60 (see FIG. 2). As the first balloon fixing member 61 and the second balloon fixing member 62, rubber bands can be used. The mounting of the rubber bands can be performed using an apparatus disclosed in JP2013-126526A, for example. Further, thread can be used as the first balloon fixing member 61 and the second balloon fixing member 62, and in this case, the balloon 60 can be fixed into the insertion part 12 by winding the first sleeve part 60A and the second sleeve part 60B with the thread.

In the above embodiment, the embodiment in which the balloon mounting jig 100 of the present invention to which the balloon is mounted is contained in the container 300 has been described, but the present invention is not limited thereto. The balloon 60 may be mounted to the insertion part 12 by using a method of inserting the insertion part 12 into the balloon mounting jig to which the balloon 60 is mounted without being contained in the container.

As described above, according to the present embodiment, in a case where the insertion part 12 of the endoscope 10 is inserted into the balloon mounting jig 100 to which the balloon 60 is mounted, the insertion part 12 can be easily moved. Further, the influence of the tension of the balloon 60 can be reduced, the balloon mounting jig 100 can be easily moved, and the balloon 60 can be easily mounted to the insertion part 12 and the insertion assisting tool.

EXPLANATION OF REFERENCES

10: endoscope
12: insertion part
14: operation part
16: universal cord
18: LG connector
20: light source device
22: cable
24: electric connector
26: processor
28: air/water supply button
30: suction button
32: shutter button
34: function switching button
36: angle knob
38: balloon air supply port
40: flexible part
42: bendable part
44: distal end part
46: forceps insertion part
48: air/water supply connector
49: suction connector
50: monitor
52: observation window
54: illumination window
56: air/water supply nozzle
58: forceps port
60: balloon
60A: first sleeve part
60B: second sleeve part
60C: balloon main body
61: first balloon fixing member
62: second balloon fixing member
64: ventilation hole
66: folded opening part
70: balloon control device 72: device main body
74: hand switch
76: pressure display unit
80: tube
82: backflow prevention unit
84: cord
86: balloon dedicated monitor
100: balloon mounting jig
102: main body
102a: first surface
102b: second surface
102c, 102d: side surface
104: first opening part
106: second opening part
108a, 108b: guide piece
110a, 110b, 110c, 110d: bent part
112: wing part
116: insertion piece
118: hole part
120: sliding surface
122: high friction part
124: low friction part
126: narrow part
128: wide part
130: restricted part
200: mounting jig mounted balloon
202: cross section
300: container
302: trunk
306: small groove part
308: container opening part
310: recess part
310a: positioning surface
310b: first restricting surface
312: flange part
312a: outer peripheral part
312b: inner peripheral part
314: lid part
318: trunk main body
320: middle groove part
322: stepped part
324: second restricting surface
S: sheet
SW1: power switch
SW2: stop switch
VIA, VIB: plan view

What is claimed is:

1. A balloon mounting jig for mounting a balloon including a balloon main body, a first sleeve part provided at one end of the balloon main body, and a second sleeve part provided at the other end on a side opposite to the first sleeve part while interposing the balloon main body, to an insertion part of an endoscope or an insertion assisting tool that assists an insertion of the insertion part of the endoscope into a body cavity, the balloon mounting jig comprising:
   a main body formed in a hollow cylindrical shape to be folded flat and having a first opening part at one end thereof and a second opening part at the other end thereof; and
   a pair of guide pieces that face each other and are provided so as to extend from the second opening part toward a side opposite to a side where the first opening part is provided,
   wherein a sliding surface on which an outer peripheral surface of the insertion part or the insertion assisting tool is slidable is provided on inner surfaces of the main body and the pair of guide pieces,
   each of the pair of guide pieces includes:
     a high friction part provided on an outer surface of each guide piece on a second opening part side; and
     a low friction part provided on an outer surface of each guide piece on a distal end side and having a smaller friction coefficient than the high friction part,
   the high friction part is a part where the second sleeve part of the balloon is retained, and
   the low friction part is a part where the first sleeve part of the balloon is retained.

2. The balloon mounting jig according to claim 1, wherein the sliding surface is a region where at least the insertion part or the insertion assisting tool is in contact with the main body and the pair of guide pieces.

3. The balloon mounting jig according to claim 2, wherein the sliding surface is an entire region of the inner surfaces of the main body and the pair of guide pieces.

4. The balloon mounting jig according to claim 1, wherein the sliding surface has a smaller friction coefficient than outer surfaces of the main body and the pair of guide pieces.

5. The balloon mounting jig according to claim 1, wherein the sliding surface is a wrinkled uneven surface.

6. The balloon mounting jig according to claim 1, wherein the sliding surface has a coating layer made of a plastic material.

7. The balloon mounting jig according to claim 1, wherein the high friction part has a smooth surface sheet or a pressure-sensitive adhesive coating layer.

8. The balloon mounting jig according to claim 1,
   wherein the pair of guide pieces each has a narrow part provided on a distal end side of each guide piece, and a wide part provided on a second opening part side of each guide piece and wider than the narrow part, and
   a total length of widths of respective wide parts of the pair of guide pieces is equal to or less than a length of an outer periphery of the insertion part or the insertion assisting tool.

9. The balloon mounting jig according to claim 1, wherein a material of the main body and the pair of guide pieces is a resin or paper.

10. A balloon mounting jig for mounting a balloon including a balloon main body, a first sleeve part provided at one end of the balloon main body, and a second sleeve part provided at the other end on a side opposite to the first sleeve part while interposing the balloon main body, to an insertion part of an endoscope or an insertion assisting tool that assists an insertion of the insertion part of the endoscope into a body cavity, the balloon mounting jig comprising:
   a main body formed in a hollow cylindrical shape to be folded flat and having a first opening part at one end thereof and a second opening part at the other end thereof;
   a pair of guide pieces that face each other and are provided so as to extend from the second opening part toward a side opposite to a side where the first opening part is provided; and
   a narrow part on a distal end side of each guide piece and a wide part wider than the narrow part on a second opening part side, which are provided in each of the pair of guide pieces,
   wherein a total length of widths of respective wide parts of the pair of guide pieces is equal to or less than a length of an outer periphery of the insertion part or the insertion assisting tool,
   the wide part includes a high friction part provided on an outer surface thereof, the narrow part includes a low friction part provided on an outer surface thereof and having a smaller friction coefficient than the high friction part, the high friction part is a part where the second sleeve part of the balloon is retained, and the low friction part is a part where the first sleeve part of the balloon is retained.

11. The balloon mounting jig according to claim 10, wherein a material of the main body and the pair of guide pieces is a resin or paper.

* * * * *